(12) United States Patent
Delenstarr et al.

(10) Patent No.: US 7,333,907 B2
(45) Date of Patent: Feb. 19, 2008

(54) SYSTEM AND METHODS FOR CHARACTERIZATION OF CHEMICAL ARRAYS FOR QUALITY CONTROL

(75) Inventors: Glenda C. Delenstarr, Redwood City, CA (US); Jayati Ghosh, Sunnyvale, CA (US); John F. Corson, Mountain View, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 0 days.

(21) Appl. No.: 11/192,680

(22) Filed: Jul. 29, 2005

(65) Prior Publication Data

US 2007/0027637 A1 Feb. 1, 2007

(51) Int. Cl.
*G06F 19/00* (2006.01)

(52) U.S. Cl. .............. 702/84; 702/22; 702/27; 436/174; 717/122; 717/131; 707/200; 714/38

(58) Field of Classification Search ............ 702/84, 702/22, 27; 436/180, 174; 435/6; 717/122, 717/131; 707/203; 714/38
See application file for complete search history.

(56) References Cited

U.S. PATENT DOCUMENTS

| | | | |
|---|---|---|---|
| 5,962,736 A * | 10/1999 | Zambias et al. ............ | 564/152 |
| 6,171,797 B1 | 1/2001 | Perbost | |
| 6,180,351 B1 | 1/2001 | Cattell | |
| 6,221,583 B1 * | 4/2001 | Kayyem et al. ............ | 435/6 |
| 6,222,664 B1 | 4/2001 | Dorsel et al. | |
| 6,232,072 B1 | 5/2001 | Fisher | |
| 6,242,266 B1 | 6/2001 | Schleifer et al. | |
| 6,251,685 B1 | 6/2001 | Dorsel et al. | |
| 6,320,196 B1 | 11/2001 | Dorsel et al. | |
| 6,323,043 B1 | 11/2001 | Caren et al. | |

(Continued)

OTHER PUBLICATIONS

GEMTools Direct Manual.Document Date: Feb. 23, 2001.

(Continued)

*Primary Examiner*—John Barlow
*Assistant Examiner*—Hien Vo

(57) ABSTRACT

Systems, methods and computer readable media for characterizing a chemical array. At least one metric indicative of accuracy of location of features on the chemical array by a feature extraction process used to extract signals from features of the chemical array may be generated, as well as additional metrics adapted to identify errors caused by a particular process used in generating the signals on the array. A quality control report may be generated to contain at least one metric indicative of accuracy of location and said at least one additional metric. Customized quality control reports may be generated by providing for user selection of at least one metric adapted to identify errors caused by a particular process used in generating signals on a chemical array, from plurality of metrics, and including such selections in the quality control report generated. Systems, methods and computer readable media are provided for characterizing a chemical array by generating metrics adapted to identify errors caused by a particular process used in generating the signals on the array, generating a quality control report containing at least one of the metrics, and outputting the quality control report.

61 Claims, 9 Drawing Sheets

U.S. PATENT DOCUMENTS

| | | |
|---|---|---|
| 6,355,921 B1 | 3/2002 | Staton et al. |
| 6,371,370 B2 | 4/2002 | Sadler et al. |
| 6,406,849 B1 | 6/2002 | Dorsel et al. |
| 6,486,457 B1 | 11/2002 | Dorsel et al. |
| 6,518,556 B2 | 2/2003 | Staton et al. |
| 2002/0102558 A1 | 8/2002 | Cattell |
| 2003/0143551 A1 | 7/2003 | Cattell |
| 2004/0094626 A1 | 5/2004 | Sillman et al. |
| 2004/0152082 A1 | 8/2004 | Troup et al. |
| 2006/0057736 A1* | 3/2006 | Peck et al. .................. 436/174 |

OTHER PUBLICATIONS

GenePix Pro microarray scanning and analysis software. http://www.axon.com/GN_GenePixSoftware.html, downloaded Sep. 20, 2004.

Welcome to BioDiscorey. http://www.biodiscovery.com/imagene.asp, dowloaded Sep. 20, 2004.

* cited by examiner

Project Run Summary /— 100

Project started on Sat, MM/DD/YYYY at 09:04:09.
Proceeding with 4 parallel execution threads S:\FE_81_Test_Images\Good Images\2x11k\Uncropped\
\US12302345_16011447011031_S01.tif
Sat Apr 09 09:04:09 2005
    *INFO:*        Grid in use: 011447_D_20050208.
    *INFO:*        Protocol in use: 22k_Linear.
    *INFO:*        multiple extractions
105         Processing array row 1, column 1.
    *WARNING:*   No Spike-in probes found in this Array -- Setting the protocol's parameter
103a  'UseSpikeIns' to false
    *ERROR:*      The grid may be placed incorrectly. The spot centroids are shifted relative
to their nominal grid.
    *WARNING:*   There are 299 (Red) negative features. Possible problem with background
107   correction method selected
    *WARNING:*   There are 579 (Green) negative features. Possible problem with
103b background correction method selected
    *ERROR:*      The grid may be placed incorrectly. There are a large number of non-
uniform or not found features along the array edges
    *WARNING:*   0 (Red) and 0 (Green) saturated features
    *INFO:*        152 (Red) and 213 (Green) feature non-uniformity outliers
    *INFO:*        38 (Red) and 8 (Green) feature population outliers
    *INFO:*        31 (Red) and 310 (Green) background non-uniformity outliers
    *INFO:*        320 (Red) and 262 (Green) background population outliers
        Processing array row 1, column 2.
    *WARNING:*   No Spike-in probes found in this Array -- Setting the protocol's parameter
'UseSpikeIns' to false
    *ERROR:*      The grid may be placed incorrectly. The spot centroids are shifted relative
to their nominal grid.
    *WARNING:*   There are 545 (Red) negative features. Possible problem with background
correction method selected
    *WARNING:*   There are 1220 (Green) negative features. Possible problem with
background correction method selected
    *ERROR:*      The grid may be placed incorrectly. There are a large number of non-
uniform or not found features along the array edges
    *WARNING:*   13 (Red) and 5 (Green) saturated features
    *INFO:*        1914 (Red) and 1916 (Green) feature non-uniformity outliers
    *INFO:*        37 (Red) and 65 (Green) feature population outliers
    *INFO:*        1665 (Red) and 1697 (Green) background non-uniformity outliers
    *INFO:*        2212 (Red) and 2247 (Green) background population outliers
S:\FE_81_Test_Images\Good Images\2x11k\Uncropped\
\US12302345_16011447010216_S01.tif
Sat MM/DD/YYYY 09:04:10

FIG. 1C

| Metric Name | $M_1$ | $M_2$ | . | . | . | . | . | . | . | . | . | . | . | . | $M_N$ |
|---|---|---|---|---|---|---|---|---|---|---|---|---|---|---|---|
| Value | $V_1$ | $V_2$ | . | . | . | . | . | . | . | . | . | . | . | . | $V_N$ |

US 7,333,907 B2

SYSTEM AND METHODS FOR CHARACTERIZATION OF CHEMICAL ARRAYS FOR QUALITY CONTROL

BACKGROUND OF THE INVENTION

Users of chemical arrays such as nucleic acid microarrays, CGH arrays, arrays measuring protein abundance and the like need software packages to perform feature extraction, that is, to extract signal and/or log ratio data from the features on the arrays. Chemical array data may have flaws due to problems in "upstream" processes such as: array synthesis; target preparation ("prep")/labeling; hybridization ("hyb")/wash; scanning; and the feature extraction algorithms used to process the data. Often the data produced is used without any quality control (QC) of such flaws by the user or the software.

Users may visually check an array to see if there are obvious flaws (e.g. streaks due to hyb/wash problems; incorrect feature positioning by the feature extraction software; etc). However, this is a very time-consuming and subjective process, not lending itself to production of metrics that can be tracked over time.

Some currently available software may report QC metrics such as overall signal level or average signal and standard deviation of signal of specific probes. However, these metrics may not cover the entire range of problems that may occur and make trouble-shooting difficult as to which upstream process may be flawed. Currently available QC software may not account for internal details of the processes to which arrays are subjected, e.g., such as array design, probe synthesis, target prep/labeling, array hyb/wash/scan and/or feature extraction. Different error modes may occur depending upon the type of processes used upstream of the data analysis step(s).

Users may have preferences to see certain metrics and not others, depending upon their experiments. Metrics may be reported without threshold warnings. Users often desire performance metrics such as "sensitivity", "dynamic range", "linearity" etc. A problem with these terms is that they can be can be defined in many different manners causing a lack of standardization across platforms and/or experiments. Additionally, these definitions may not be appropriate for all array experimental conditions.

Users may have difficulties in interpreting array data due to incorrect algorithms being used (e.g. background-subtraction, dye-normalization algorithms and the like) and not have metrics that readily aid in this type of evaluation.

There remains a need for quality control solutions for objectively determining the quality of chemical arrays covering a variety of different experiments and different experimental conditions employed that may require a variety of different metrics to be employed to identify errors, or lack thereof, that may occur when using any of these variety of conditions and experiments. A variety of metrics are needed to capture a wide range of potential upstream process problems that can affect the quality of a chemical array produced by such processes.

SUMMARY OF THE INVENTION

Methods, systems and computer readable media for generating at least one metric indicative of accuracy of location of features on a chemical array by a feature extraction process used to extract signals from features of the chemical array; generating at least one additional metric adapted to identify errors caused by a particular process used in generating the signals on the array; and generating a quality control report containing said at least one metric indicative of accuracy of location and said at least one additional metric.

Methods, systems and computer readable media for generating a customized quality control report, to include user selection of at least one metric adapted to identify errors caused by a particular process used in generating signals on a chemical array, said at least one selection being selected from a plurality of metrics; and generating a quality control report containing the at least one user-selected metric.

Methods systems and computer readable media for characterizing a chemical array are included. Means for generating metrics adapted to identify errors caused by a particular process used in generating the signals on the array are provided, as well as means for generating a quality control report containing at least one of the metrics. Means for outputting the quality control report are provided.

These and other advantages and features of the invention will become apparent to those persons skilled in the art upon reading the details of the systems, methods and computer readable media as more fully described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1C shows a portion of a project run summary that summarizes processing information for a batch run of arrays, and may include error statements, warning statements and/or additional summary information. Note that a run summary may also be provided when only a single array is processed.

DETAILED DESCRIPTION OF THE INVENTION

Figure 1A:
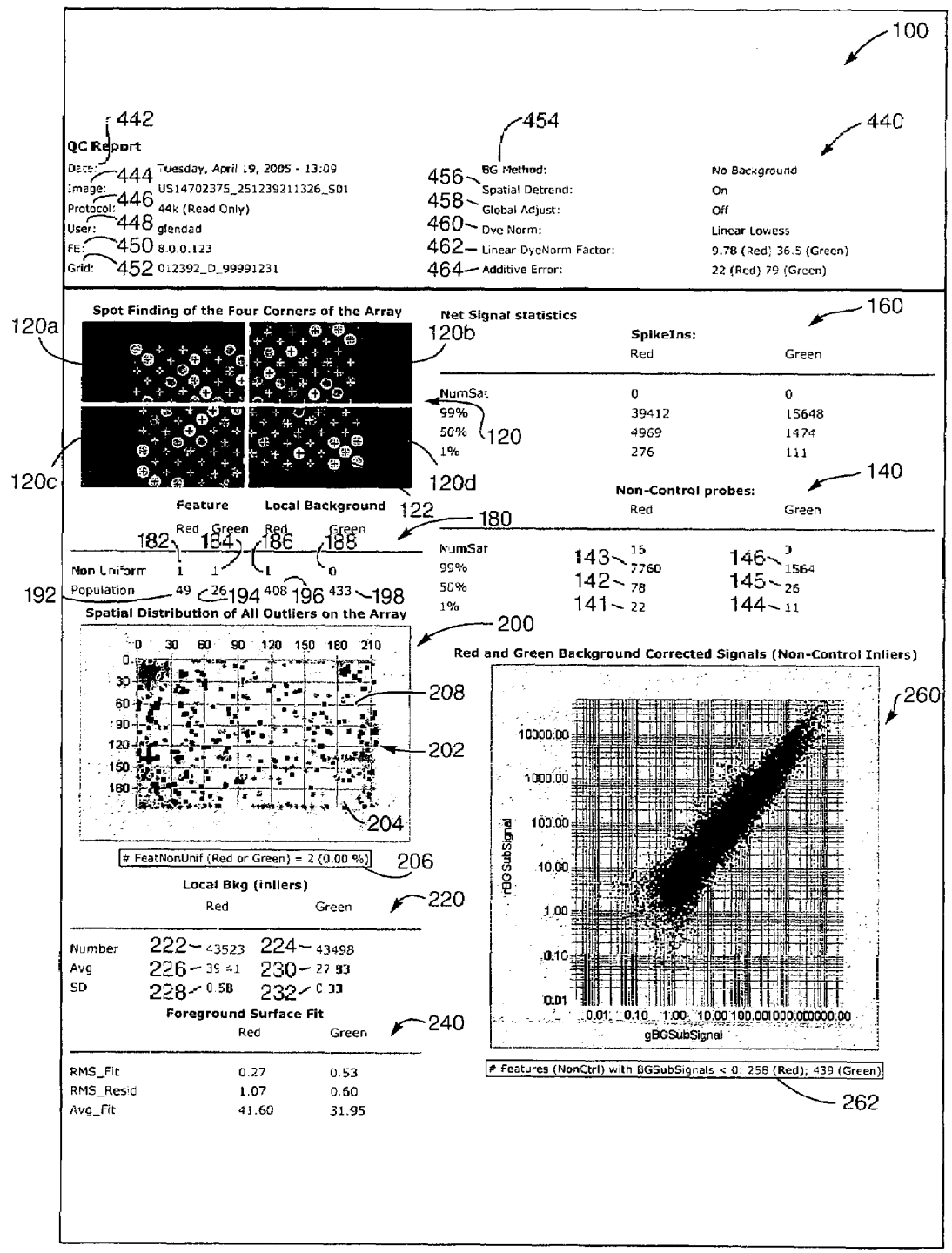
FIGS. 1A-1B show an example QC report that may be outputted according to the present systems and methods.

Before the present systems, methods and computer readable media are described, it is to be understood that this invention is not limited to particular systems, methods and computer readable media described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a feature" includes a plurality of such features and reference to "the array" includes reference to one or more arrays and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

A "chemical array", "microarray", "bioarray" or "array", unless a contrary intention appears, includes any one-, two-or three-dimensional arrangement of addressable regions bearing a particular chemical moiety or moieties associated with that region. A microarray is "addressable" in that it has multiple regions of moieties such that a region at a particular predetermined location on the microarray will detect a particular target or class of targets (although a feature may incidentally detect non-targets of that feature). Array features are typically, but need not be, separated by intervening spaces. In the case of an array, the "target" will be referenced as a moiety in a mobile phase, to be detected by probes, which are bound to the substrate at the various regions. However, either of the "target" or "target probes" may be the one, which is to be evaluated by the other.

Methods to fabricate arrays are described in detail in U.S. Pat. Nos. 6,242,266; 6,232,072; 6,180,351; 6,171,797 and 6,323,043. As already mentioned, these references are incorporated herein by reference. Other drop deposition methods can be used for fabrication, as previously described herein. Also, instead of drop deposition methods, photolithographic array fabrication methods may be used. Interfeature areas need not be present particularly when the arrays are made by photolithographic methods as described in those patents.

Following receipt by a user, an array will typically be exposed to a sample and then read. Reading of an array may be accomplished by illuminating the array and reading the location and intensity of resulting fluorescence at multiple regions on each feature of the array. For example, a scanner may be used for this purpose is the AGILENT MICROARRAY SCANNER manufactured by Agilent Technologies, Palo, Alto, Calif. or other similar scanner. Other suitable apparatus and methods are described in U.S. Pat. Nos. 6,518,556; 6,486,457; 6,406,849; 6,371,370; 6,355,921; 6,320,196; 6,251,685 and 6,222,664. Scanning typically produces a scanned image of the array which may be directly inputted to a feature extraction system for direct processing and/or saved in a computer storage device for subsequent processing. However, arrays may be read by any other methods or apparatus than the foregoing, other reading methods including other optical techniques or electrical techniques (where each feature is provided with an electrode to detect bonding at that feature in a manner disclosed in U.S. Pat. Nos. 6,251,685, 6,221,583 and elsewhere).

A "design file" is typically provided by an array manufacturer and is a file that embodies all the information that the array designer from the array manufacturer considered to be pertinent to array interpretation. For example, Agilent Technologies supplies its array users with a design file written in the XML language that describes the geometry as well as the biological content of a particular array.

A "grid template" or "design pattern" is a description of relative placement of features, with annotation. A grid template or design pattern can be generated from parsing a design file and can be saved/stored on a computer storage device. A grid template has basic grid information from the design file that it was generated from, which information may include, for example, the number of rows in the array from which the grid template was generated, the number of columns in the array from which the grid template was generated, column spacings, subgrid row and column numbers, if applicable, spacings between subgrids, number of arrays/hybridizations on a slide, etc. An alternative way of creating a grid template is by using an interactive grid mode provided by the system, which also provides the ability to add further information, for example, such as subgrid relative spacings, rotation and skew information, etc.

A "grid file" contains even more information than a "grid template", and is individualized to a particular image or group of images. A grid file can be more useful than a grid template in the context of images with feature locations that are not characterized sufficiently by a more general grid template description. A grid file may be automatically generated by placing a grid template on the corresponding image, and/or with manual input/assistance from a user. One main difference between a grid template and a grid file is that the grid file specifies an absolute origin of a main grid and rotation and skew information characterizing the same. The information provided by these additional specifications can be useful for a group of slides that have been similarly printed with at least one characteristic that is out of the ordinary or not normal, for example. In comparison when a grid template is placed or overlaid on a particular microarray image, a placing algorithm of the system finds the origin of the main grid of the image and also its rotation and skew. A grid file may contain subgrid relative positions and their rotations and skews. The grid file may even contain the individual spot centroids and even spot/feature sizes. Further information regarding design files, grid templates, design templates and grid files and their use can be found in co-pending, commonly owned application Ser. No. 10/946,142 filed Sep. 20, 2004 and titled "Automated Processing of Chemical Arrays and Systems Therefore. Application Ser. No. 10/946,142 is hereby incorporated herein, in its entirety, by reference thereto.

A "history" or "project history" file is a file that specifies all the settings used for a project that has been run, e.g., extraction names, images, grid templates protocols, etc. The history file may be automatically saved by the system and, in one aspect, is not modifiable. The history file can be employed by a user to easily track the settings of a previous batch run, and to run the same project again, if desired, or to start with the project settings and modify them somewhat through user input. History files can be saved in a database for future reference.

"Image processing" refers to processing of an electronic image file representing a slide containing at least one array, which is typically, but not necessarily in TIFF format, wherein processing is carried out to find a grid that fits the features of the array, e.g., to find individual spot/feature centroids, spot/feature radii, etc. Image processing may even include processing signals from the located features to determine mean or median signals from each feature and may further include associated statistical processing. At the end of an image processing step, a user has all the information that can be gathered from the image.

"Post processing" or "post processing/data analysis", sometimes just referred to as "data analysis" refers to processing signals from the located features, obtained from the image processing, to extract more information about each feature. Post processing may include but is not limited to various background level subtraction algorithms, dye normalization processing, finding ratios, and other processes known in the art.

A "protocol" provides feature extraction parameters for algorithms (which may include image processing algorithms and/or post processing algorithms to be performed at a later stage or even by a different application) for carrying out feature extraction and interpretation of data from an image that the protocol is associated with. A protocol may also have user preferences regarding a QC Report which may be used as a summary of overall metrics measured and/or calculated, or a subset of metrics. Such preferences may specify which metrics are reported in the QC Report, for example, type of metrics, specific metrics to report, or specify that only metrics that pass or fail some user-defined threshold are reported. Other preferences may specify which type of QC Report is to be produced, for example, a two-channel (two-color) or single channel (single color) report. Additionally, specified types may include Gene Expression, CGH, Location Analysis, etc. Protocols are user definable and may be saved/stored on a computer storage device, thus providing users flexibility in regard to assigning/pre-assigning protocols to specific microarrays and/or to specific types of microarrays. The system may use protocols provided by a manufacturer(s) for extracting arrays prepared according to recommended practices, as well as user-definable and savable protocols to process a single microarray or to process multiple microarrays on a global basis, leading to reduced user error. The system may maintain a plurality of protocols (in a database or other computer storage facility or device) that describe and parameterize different processes that the system may perform. The system also allows users to import and/or export a protocol to or from its database or other designated storage area.

An "extraction" refers to a unit containing information needed to perform feature extraction on a scanned image that includes one or more arrays in the image. An extraction includes an image file and, associated therewith, a grid template or grid file and a protocol.

A "feature extraction project" or "project" refers to a smart container that includes one or more extractions that may be processed automatically, one-by-one, in a batch. An extraction is the unit of work operated on by the batch processor. Each extraction includes the information that the system needs to process the slide (scanned image) associated with that extraction.

When one item is indicated as being "remote" from another, this is referenced that the two items are not at the same physical location, e.g., the items are at least in different buildings, and may be at least one mile, ten miles, or at least one hundred miles apart.

"Communicating" information references transmitting the data representing that information as electrical signals over a suitable communication channel (for example, a private or public network).

"Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer. Where the processor is programmable, suitable programming can be communicated from a remote location to the processor, or previously saved in a computer program product. For example, a magnetic or optical disk may carry the programming, and can be read by a suitable disk reader communicating with each processor at its corresponding station.

Reference to a singular item, includes the possibility that there are plural of the same items present.

"May" means optionally.

Methods recited herein may be carried out in any order of the recited events which is logically possible, as well as the recited order of events.

All patents and other references cited in this application, are incorporated into this application by reference except insofar as they may conflict with those of the present application (in which case the present application prevails).

The present invention provides a variety of metrics that provide objective measurements adapted to capture a wide range of potential upstream process problems that may affect the quality of a chemical array produced by such processes. Such metrics may be calculated, plots made and posted to a QC Report which may be used as a summary of overall metrics measured and/or calculated, or a subset of metrics. Errors 103 and warnings 105 (e.g., if metrics are over a given threshold) may be shown in a text-based run summary 101 (e.g., see FIG. 1C), and all values (but not graphical plots) may be contained in a larger statistics table in the textual output which may also contain raw feature extraction measurements. The calculation of metrics is objective and produces values that can be tracked over time (e.g. using a compilation of statistics table outputs). As discussed below, the content of which metrics are displayed in the QC Report can be customized by a user. In addition, the QC report and run summary can be further customized to show only those metrics and/or errors and/or warnings for metrics that exceed a user-settable (or calculatable) threshold.

The metrics calculated may make use of knowledge of specific processes, when known, including, but not limited to those used in probe selection, synthesis, target preparation (including, but not limited to processes such as labeling, amplification and the like), hyb, wash and/or stripping procedures, scanning, and feature extraction of chemical arrays. A subset of metrics provided are more generic for quality control of those chemical arrays for which specific processes are not known. Metrics may be calculated with customized filters of the data, in order to make use of knowledge of specific processes and to make the metrics more specific.

Metrics may exclude a consideration of features based upon one or more filters that can be applied. One such filter determines if a feature or background region is non-uniform and/or a population outlier, and the system is configured to automatically flag such non-uniform features and population outliers. Further, metrics may be adapted to filter features to consider specific sequence types of features as a basis for a metric calculation. For example, metrics include filters to consider only one, or a specified number of the probes types including positive controls, negative controls, spike-in controls and experimental probes (i.e., "non-control probes"). In addition, in one aspect, the software of the system is designed to be modifiable to allow changes to control types that may be filtered and/or identification of sub-types of probes for filtering purposes. Further, filtering may be implemented to consider a specified feature signal range and/or a specified log-ratio significance level. Still further, for those metrics that calculate summary statistics (e.g., averages, standard deviations, etc.) based upon a population of features or background regions, the user can set, in the protocol, the minimum number of features or background regions that need to be present in order to allow the calculation of such summary statistics. Indeed, all the above filters may be user-customizable.

One or more figures, charts and/or plots may be generated and outputted in the QC report to give users a quick and reproducible visual representation of processes which may not have simple numeric metrics. Examples include, but are not limited to: plots of array rows versus columns showing positions where features and/or local background have been flagged as outliers (e.g., non-uniform outliers or population outliers). As noted above, these outliers may be calculated automatically by the system during feature extraction. Plotting the locations of the same provides a quick and systematic visual tool by which a user can rapidly view outlier problems that may exist with each chemical array, without the need for a user to manually inspect the full image of each array, which can be tedious, time consuming and error-prone. By identifying and plotting only such outliers, the user does not have to visually parse these from a field of otherwise "good" features and background levels. This can provide a great time savings, particularly when arrays are processed in batch mode, which is more and more becoming the norm in many institutions. Additionally, this provides a more objective measure of the outliers, since the ability of a user to visually discern outliers when "buried" in the full view among "good" features and background levels (i.e., non-outliers) may vary greatly. Also, users tend to fatigue or become less attentive after viewing a number of full images and error rates may tend to increase with an increasing number of images from a batch of arrays to review.

A composite image of the four corners of a chemical array may be extracted from the full image of the array and presented in the QC report with centers of centroids shown that are calculated by the feature extraction process. By displaying only the four corners, a user may readily assess problems that the feature extraction process may have had in locating the feature positions on the chemical array. Such an image provides a much less congested visualization, with less information overload to the user when viewing, so that a quicker and more systematic manner of viewing problems in feature location is provided, compared to the manual viewing of each full image by the user. Generally, a confirmation that features in all four corners of the array have been properly positioned provides an acceptable level of confidence that all features within the four corners and which are not shown in the composite image, were also properly located, and that it is rare to have an array where the features in the four corners were properly located, but those features located inside the four corners were not.

Numeric values of metrics can be compared to thresholds and warnings shown for those that are over or under given thresholds. Thresholds can be obtained in several manners, including, but not limited to the following examples. When chemical arrays are provided for which the entire chain of production processes is known, the feature extraction component of the system may include lists of thresholds that are appropriate for different specified groups of processes, and these lists can be updated, as needed. Alternatively, users may supply their own lists of thresholds that can be used by the feature extraction component. Further alternatively, users may employ data stored in a database to generate run charts and thereby generate customized threshold lists based upon such data. Further information regarding generating threshold data from run charts in disclosed in co-pending, commonly owned Application Ser. No. 11/193,912 file concurrently herewith and titled "CGH Array Quality Assessment". Application Ser. No. 11/193.912 is hereby incorporated herein, in its entirety, by reference thereto.

Users may customize the QC report by selecting which metrics are to be shown in the QC Report. A user's selection can be saved and used later with other arrays (or same array with different feature extraction algorithm settings). Multiple lists may be maintained to support different QC metric lists, depending upon experimental variables. A list may be dynamic. For example, the QC Report may only show those metrics that exceed thresholds and/or prompt warnings. Regardless of which metrics are chosen for the QC Report, the system produces a statistics table file that includes all numeric metrics calculated. User preferences may be saved in a database for retrieval to apply to future extraction processing.

Further customization of the system may be saved as user preferences, including, but not limited to: selection of colors in which plots are displayed (for example, plots that typically shows colors in red and green can be viewed in other colors, such as blue and yellow, in order to assist viewing by users with color blindness); type of file format in which data is to be saved (e.g., PDF, HTML, etc.); type of report to be generated (e.g., inspection of nucleic acid array, inspection of CGH array, inspection of single-color array, location analysis, etc.); and/or information to be printed in the header of the QC report, details of which are further described below.

The system may automatically exclude the reporting of metrics that are not appropriate to the chemical array being reported on. For example, if the array has no spike-in probes listed in the grid template, or if the user of the array did not use spike-in target (as determined by a user-settable parameter in the protocol, or determined by the software), then metrics characterizing spike-ins will not be reported in the QC report. Further, even if the user did select to report such metrics in the protocol, the metrics characterizing spike-ins will not be reported if the probes are not found in the grid template. This situation may also generate a warning message 105 in the run summary 101, e.g., "WARNING: No Spike-in probes found in this array—Setting the protocol's parameter 'UseSpikeIns' to false". If the array being considered is a single-channel array, then log-ratio metrics will automatically not be shown in the QC report.

If the array being considered is a single-channel array, then log-ratio metrics will automatically not be shown in the QC report 100. Other types of metrics and patterns of metrics (e.g., which metrics to report or not to report) may be used for other array platforms, such as CGH or Location Analysis.

Although performance metrics are calculated that represent a given definition of concepts such as "sensitivity", "dynamic range", and "linearity", these metrics are not absolute values of sensitivity, dynamic range and linearity to be compared across different array platforms. Rather, they are relative values that are calculated consistently and can be tracked in a relative manner to look for changes to these values.

By studying groups of metrics, one can differentiate between different types of process problems. For example, errors in array synthesis will give a different pattern of metrics than errors in the array hyb, wash, and/or stripping processes or other processes involved in generating signals from features on an array. Metrics may be calculated for specific use in evaluating different choices of algorithms. For example, such metrics may help to determine which background-subtraction method or dye-normalization method is best or appropriate for a given experimental process.

By providing a broad range of metrics, the present system facilitates the identification of many different potential error modes in the processing of arrays that lead to defects. Such metrics are objective, and numeric metrics that are provided can be tracked over time. The analysis of such tracking can establish thresholds of acceptable quality, such as average values, standard deviations, error bars, and identification of those arrays that fail to perform with acceptable parameters established by the time series analysis of such metrics.

Customized metrics, when specifics of array production processes are known, provide an even more sensitive evaluation that may more specifically target sources of errors. The figures and graphics that may be provided in the QC report are capable of providing more complex array quality control where it is possible to visualize systemic errors in the production of an array. The metrics produced may be compared to thresholds, either provided by the system or the user. Users can customize the metrics shown in the QC report to view and save these preferences. Performance metrics such as sensitivity, dynamic range, and linearity are robust and well-defined.

Different error modes may be differentiated by different patterns of metric values. Customized metrics may be produced that allow the evaluation of different choices of feature extraction algorithms (often referred to as "parameter tuning"). To use these metrics, the user can feature extract one array with many types of algorithms and by evaluation of the specific metrics, determine which algorithm is correct for their system.

Figure 1B:
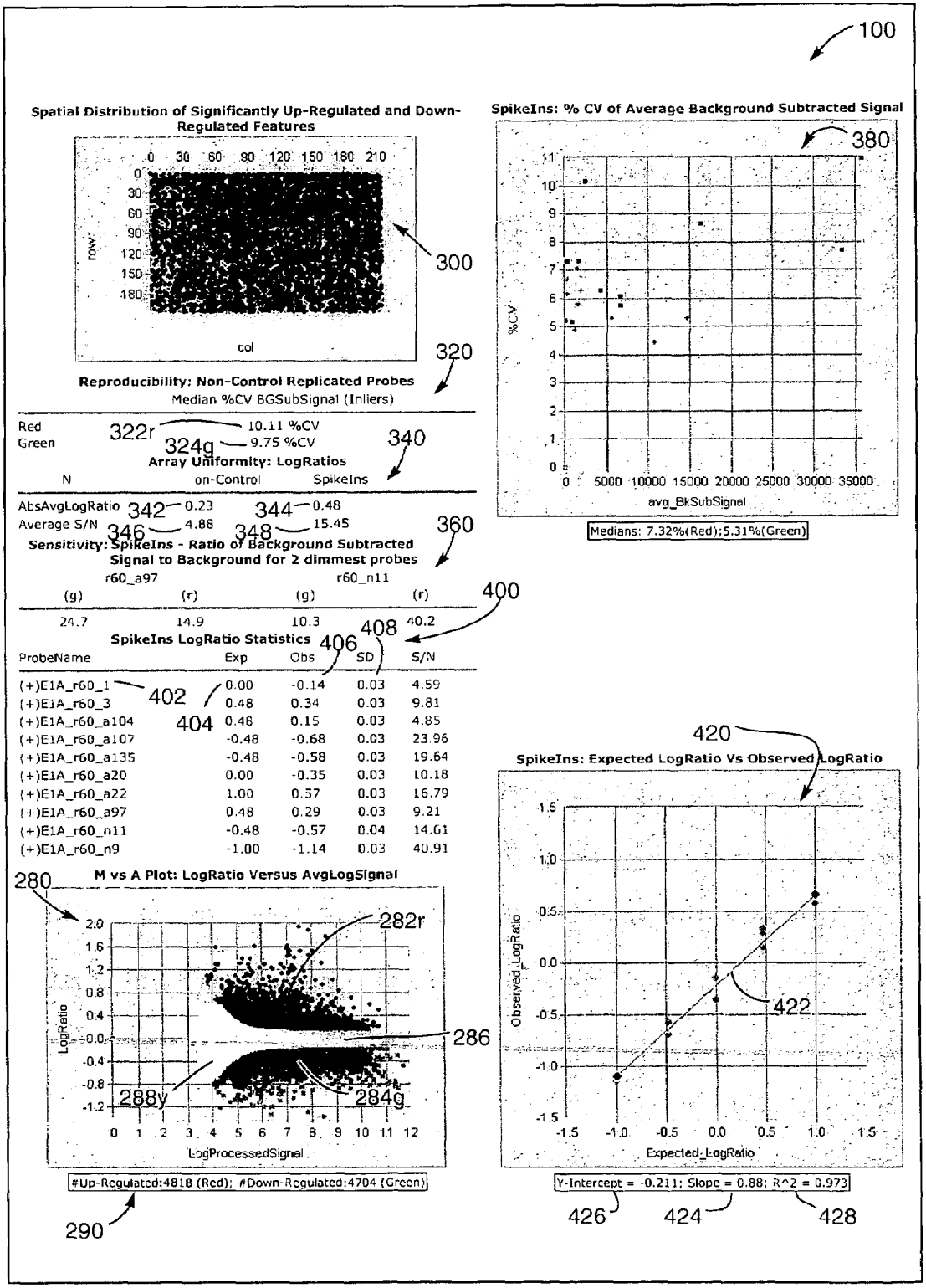

Turning now to FIGS. 1A-1B, an example of a QC report 100 as outputted by the present systems and methods is shown. The system generates metrics characterizing a chemical array based on feature extraction outputs from an existing feature extraction component of the system and generates a QC file containing pre-designated metrics, according to methods described herein. The QC file may be outputted as QC report 100 for visualization and review by a user to observe objective characterizations of the chemical array being considered, to aid in determining the quality and/or potential error sources causing quality defects in the resultant array. Such output may be a visualization on a display, such as the display of a user interface, for example, and/or a hard copy printout of QC report 100 on paper or other physical medium, including computer readable media such as removable storage disks, hard disks, floppy disks, CD or DVD disks, etc.

QC report 100 may contain a variety of metrics designed to facilitate the identification of many different potential error modes in the processing of arrays that lead to defects. QC report 100 may contain at least one metric indicative of accuracy of location of features by a feature extraction process used to extract signals from features of the chemical array and at least one additional metric adapted to objectively identify errors caused by a particular process relating to array design processes, array synthesis processes, target preparation processes, target labeling processes, array hybridization processes, washing processes, scanning processes or feature extraction processes.

Figure 2:
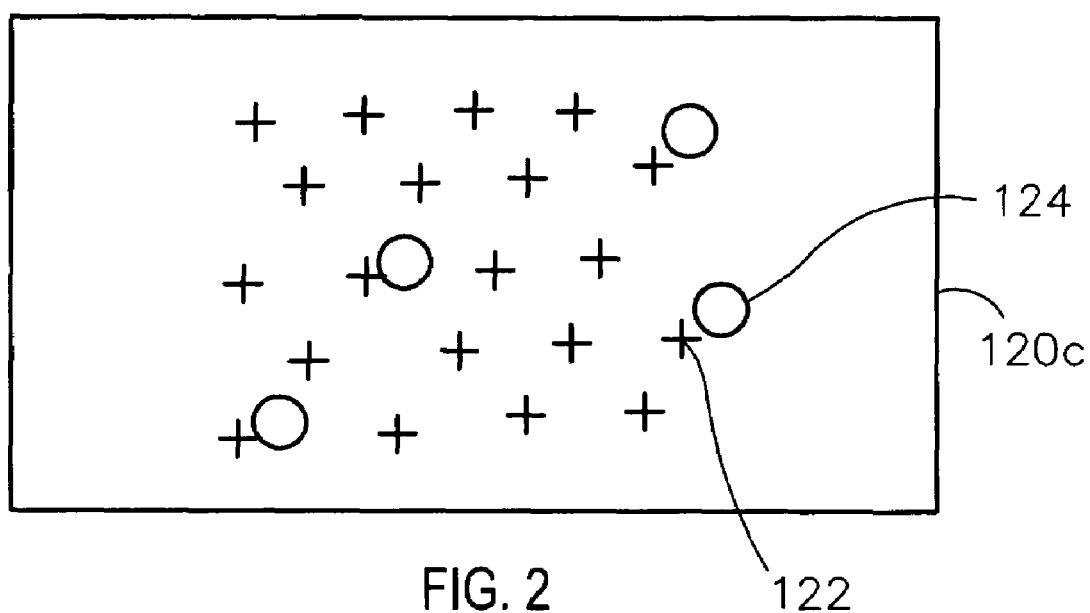
FIG. 2 shows an example of a graphical metric indicative of accuracy of location of features by a feature extraction process used to extract signals from features of the chemical array.

Metric 120 provides a visualization of the four corner portions 120a, 120b, 120c, 120d of a chemical array that is being evaluated for quality by the present system. A composite image 120 of the four corners of a chemical array may be extracted from the full image of the array and presented in QC report 100 with centers of centroids 122 shown that are calculated by the feature extraction process. By displaying only the four corners, each typically with about twenty±ten features 124, e.g., see FIG. 2 (although this metric is not limited to this number of features per corner, as more or fewer may be used), and by showing some of the space outside of the features of the array, a user may readily assess problems that the feature extraction process may have had in locating the feature positions on the chemical array, by comparing the plotted centers of centroids 122 to the images of the features 124. In the example shown in FIG. 1A, the feature extraction grid used to place centroids 122 on features 124 appears to have been properly placed. However, if the visualization shows placement of centroids 122 in any or all corners 120a, 120b, 120c, 120d that are off center, or totally misaligned with features 124, such as in the example of corner 120c shown in FIG. 2, then a user can readily visually identify that there has been a problem with grid alignment during feature extraction and go back and manually correct the alignment (or use another grid alignment algorithm) and reprocess the feature extraction, then allow the system to generate another QC report and again visually review metric 120. Although not shown in FIG. 1A or 2, cookie placement by the feature extraction process may also be visualized in this metric to show cookie placement relative to the images of the features, where the "cookie" is a shape drawn on the feature showing the area of pixels that was extracted to yield signal for that feature.

Image 120 provides a much less congested visualization, with less information overload to the user when viewing (since the image of the full array typically shows about 20,000 to 40,000 features), so that a quicker and more systematic manner of viewing problems in feature location is provided, compared to the manual viewing of each full image by the user. Further, when the full image is presented, it is necessarily in a smaller scale, so that often, if a user does think that he or she has identified a misalignment, it is often necessary to zoom in on the location of perceived misalignment to visually verify it, which is even more time consuming and tedious. The advantages noted are even more apparent with batch processing, since a user can become easily fatigued or distracted when faced with having to visually examine fifty full array images each containing 20,000 features, for example. Further, generally a confirmation that features in all four corners of the array have been properly positioned provides an acceptable level of confidence that all features within the four corners and which are not shown in the composite image, were also properly located, and that it is rare to have an array where the features in the four corners were properly located, but those features located inside the four corners were not. As discussed below, numeric metrics may also be calculated that give an indication of the "goodness of fit" of the grid on the array. Also, error messages, such as 103*a* and 103*b* may be reported in run summary 101 (FIG. 1C) if one or more of these metrics exceed a given threshold.

The system is capable of discriminating between different types of probe signals and calculating metrics based on only signals from a particular type of probe. The most discrimination is available when specifics of array production processes are known. For example, users often want to know what the dynamic range of the signals extracted from a chemical array is. The system is capable of providing very specific accurate metrics to satisfy this inquiry. Typical reports indicate a signal value from the lowest five percentile of the signal range and a signal value from the ninety-fifth percentile. The present system is capable of reporting the signal value from the one percentile and ninety-ninth percentile, respectively, but, more importantly, the present system does not add up all the signals to obtain the reported values, but considers only certain types of probes, such as the non-control ("experimental") probe signal values, and not the negative control values, and/or the positive-control values that depend upon what types of positive spike-ins are used if any.

For example, spike-in target molecules may be added to a sample prepared on a chemical array to assess any degradation in the overall performance of the array (including, but not limited to sensitivity, reproducibility, signal to noise, dynamic range, linearity of response, and background metrics). Such spike-in molecules may comprise sequences that bind, under the employed hybridization conditions, to probes with complementary sequences at pre-defined positions within the array layout. A plurality of probe features may be provided on an array, which are complementary to a plurality of spike-in molecules. Such plurality of spike-in molecules may comprise defined sequences present in different amounts in the two channels and thus, that have known ratios between the channels ("expected ratios"). The complexes formed between spike-in molecules and complementary probe sequences should be present and ratios calculated by the system in the same relative ratios as the expected ratios, thereby providing a mechanism to assess the performance of the array after a hybridization and/or stripping process. Alternatively, such as with single-color array analysis, for example, the spike-in sequences may have a known ratio of concentration (e.g., "copy number") with respect to each of the spike-in sequences in the hybridization mixture. In such a case, the system analyzes the observed ratio of signals between sequences in a given channel and compares them to the expected ratios. In one aspect, a spike-in sequence is complementary to an adenovirus type 5 E1a sequence (e.g., nucleotides 560-972 or a subsequence thereof). In another aspect, synthetic transcripts are spiked into a total RNA sample at different ratios for each channel. Spike-in ratios should be preserved in the complexes formed between the spike-in transcripts and complementary probe targets included on the array.

Negative control signal values, as well as positive control signal values, such as spike-in values clearly can skew the reported dynamic range values, so they are not considered when reporting signal values characterizing the experimental sample probes. These non-control probes values may be reported in tabular form 140 as shown in FIG. 1A. For single-channel, two-channel, or multiple channel (i.e., more than two channels) arrays, the signal values are reported separately with respect to each channel. In the example shown, first, fiftieth and ninety-ninth percentile values are reported for each of red and green channel, i.e., 141, 142, 143 and 144, 145, 146, respectively. The percentile ranges, or other types of summary statistics of signal (e.g., averages, standard deviations and/or inter-quartile ranges, etc.) may be reported, as customized by the user, The signals analyzed may be raw mean signals, but are typically the "net signals", which are the mean signals (extracted for each feature) minus the scanner offset. In this manner, the resulting net signal is independent of the version of scanner used to scan the array image.

If spike-in probes are present on the array being reported on, the system may automatically also report dynamic ranges of spike-in probe signals in metric 160, or such report may be selected by a user preference indicating the presence of spike-in probes, discussed below. As is readily apparent, the high end of the signal values for spike-in probes show values that are much higher than the respective high ends of the non-control signal values. Thus, if all the probe types had been considered together (as is typically done by current methods), the reported dynamic range of the signal values for the experimental probes would be skewed significantly upward for this example.

In one aspect, the feature extraction module of the system provides automatic flagging of features and local background regions that are determined to be non-uniform, such as by being significantly out of round (features), containing donuts (features), crescents (features), bright spots (features or local background), dark spots (features or local background), scratches (features or local background), incomplete wash (features or local background), incomplete stripping (e.g., where an array is being or has been stripped for reuse), or other imperfections that would render the signal therefrom unreliable. By tabulating the flagged outputs from the feature extraction, the system may generate a metric 180 that indicates to the user the total number of non-uniform features (182 and 184, respectively) with respect to each channel, as well as the number of flags indicating locations of non-uniform local background levels (186 and 188, respectively). The number of non-uniform features may be used to detect array synthesis flaws. The number of non-uniform features and population outliers for features and local backgrounds may be used to detect hyb/wash artifacts and/or other defects in procedures used to generate signals at features on the array.

Figure 3:
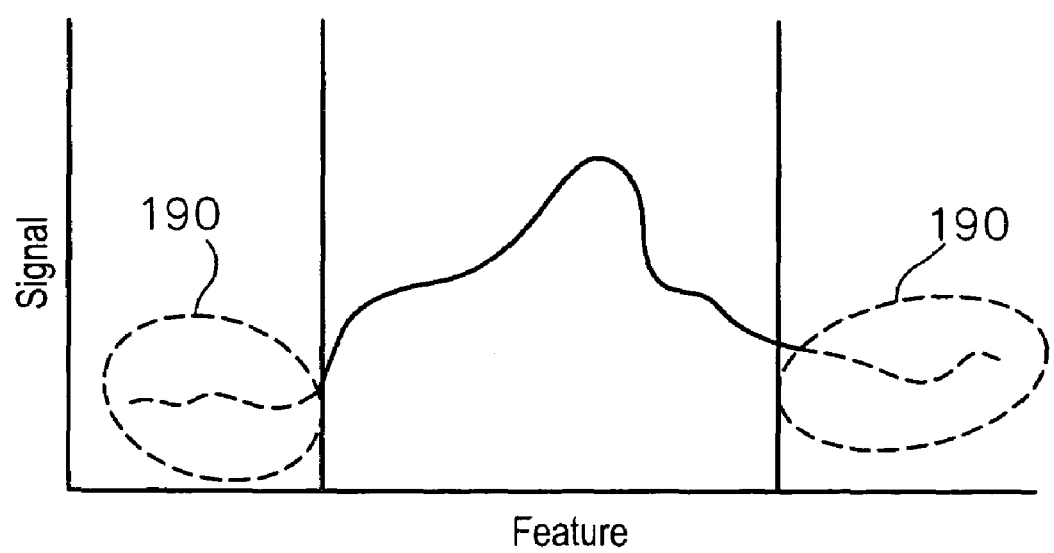
FIG. 3 illustrates plotting of signals in a histogram to identify population outliers.

Additionally, both feature and local background population outliers are identified by the feature extraction module. Signals from all uniform features are plotted as illustrated in FIG. 3, and a lower and upper threshold may be calculated from those uniform features. The calculated thresholds may then be used to flag any feature (whether or not it has been previously flagged as non-uniform) as a population outlier 190 if that feature's signal is outside (less than or greater then, respectively) the lower or upper threshold. Signals from local background are plotted similarly and population outliers for the local background are similarly determined. The system counts the number of population outliers identified by feature extraction and reports the same for each channel, for both features and local background as shown in metric 180 (see 192, 194, 196 and 198).

In addition or as an alternative to the numeric metric 180 identifying non-uniform and population outlier features and local background locations, the system may provide a graphical metric 200 to identify such problems in a composite manner. Graphic metric 200 provides a visual representation of the spatial locations of the identified non-uniform locations and population outliers which can be extremely useful to a user to rapidly identify trends in such errors. For example, if the representation of these errors increases going from left to right over the chemical array visualization 202, this may indicate a gradient error over the array, a concentration of errors in one location may indicate an incomplete wash or hybridization error in that area, an irregular line of errors may identify a scratch on the array, etc.

In one aspect, to generate plot 200, the system evaluates the results of eight values for each feature position, for a two-channel system (or, more generally, 4×N values, where N=the number of channels on the array) to determine, with respect to each location (feature and local background locations), whether a flag has been set to indicate an error. In certain aspects, the values considered are the values reporting flags for non-uniform features, non-uniform local background, population outlier features, and population outlier local background, for each channel (red and green in this example). In one aspect, for any given location, if a flag has been set in any of the eight values, the system plots a spot 204 on the location of the array visualization 202 corresponding to or representing the actual location on the array as determined by the feature extraction. If a flag appears in any of the green channel files, the spot is visualized as a green spot and conversely, if a flag appears in any of the red channels, then a red spot is represented on the array visualization 202 in metric 200. If at least one flag occurs in each of the channels, then a third color may be used for a representative spot, e.g., blue, or other color, which may be user settable. Alternatively, either of the colors assigned to the first and second channels may be designated as a default color to be displayed when a flag occurs in each channel.

Metric 200 provides an overall, nonspecific view of where all outliers and non-uniformities exist on the chemical array being reported on. By viewing metric 200, a user can rapidly get an overall visualization of the pattern of the outliers and non-uniformities on the array. The metric is non-specific in that the user can not identify from metric 200 whether any particular spot 204 represents a non-uniformity or a population outlier, or whether such non-uniformity or population outlier represents a feature or local background, but through repeated use, a user will begin to identify certain patterns as indicative of certain types of errors. For example, those spots 204 around the perimeter of the array 202 are typically attributable to local background population outliers, and other particular patterns develop to identify non-uniformities. Alternatively, the user settable features allow a user to plot multiple metrics 200, e.g., where one of such metrics plots only population outliers and another of such metrics 200 plots only non-uniformities. Further alternatively, the QC report 100 may be set to plot only one metric 200 that plots either non-uniformities only or population outliers only. Further alternatively, the QC report 100 may be set to plot metric 200 in separate plots for features and local background regions, respectively. Further alternatively, the QC report 100 may be set to plot flags in only one channel, if the QC report is a "single-channel" type of report. Additionally, metric 200 may serve as a first alert, so that if a user does note an unusual pattern of spots 204, the user can go to the full image of the chemical array resulting from the scan of the array, and visually review it and zoom in on locations identified by metric 200 for a closer, more complete examination.

Additionally, metric 200 may provide a numeric display of the total number of feature non-uniformities 206 with a calculated percentage that this number represents relative to the total number of features. In the example shown, the number of non-uniform features was only two and the percentage was calculated as 0.00% (2 out of 43,931 features=0.0046% (shown in the textual statistics table, while rounding to 0.00% is for purposes of display in QC report 100). Grid lines 208 may also be superimposed on the array visualization 202 to assist the user in identifying locations of spots 204 relative to the overall array.

Another advantage of flagging outliers using the feature extraction module is that the system can also report a metric 220 identifying the population statistics of the local background inliers. By excluding outliers, more accurate data relating to the useable signals (e.g., such as statistical data) can be provided. Metric 220 reports numeric information after the system counts the total number of local background inliers for each channel (reports at reference numerals 222 and 224, respectively, in the example shown in FIG. 1A). Additionally, the average signal and standard deviation of the local background inlier signals for each channel may be calculated and reported (226, 228, 230 and 232, respectively). This metric is useful for describing signal distribution for different types of backgrounds, and may be useful to detect hyb/wash and/or stripping artifacts and low signal noise, for example.

When a de-trending algorithm is applied during feature extraction, statistics representing the foreground surface fit may be reported by the system in metric 240, where "foreground" represents background-level signal that is present on features. From viewing these statistics, the user can get an idea of how much of a foreground surface was detected by the system, and how well the de-trending algorithm performed to provide a foreground surface fit. An alternative set of algorithms, including de-trending algorithms may be provided for detecting and removing gradients of signal present at higher signal ranges, often referred to as "multiplicative detrending". These types of algorithms are especially important in single-channel array analyses.

Additionally, the system may provide a metric 260 plotting background subtracted signals of one channel versus another channel (in this case, background subtracted red signals versus background subtracted green signals). The system filters the signal data prior to generating the plot to remove control signals and outliers (e.g., non-uniform features and saturated features), so that only inlier feature signals are plotted. Since plot 260 is generated on a log scale, background subtracted signals that result in a negative signal value cannot be plotted, since the log of such a value cannot be calculated. Accordingly, the system counts the number of background-subtracted signals of all features, or of only non-control features, in each channel that have a negative value and reports 262 these numbers, as an indicator of signal values that cannot be shown on the plot 260. This numerical report 262 can be useful to show when a particular array has significant background errors, and/or in instances where a user may be experimenting with changing the background default settings of the feature extraction software to try and optimize background processing settings. This may be accomplished by extracting a given image, or set of images, multiple times, while varying the background processing parameters during different extractions. By comparing the reported number of negative background signals reported for a given image among multiple extractions having different background extraction settings, a user can observe, by a substantial increase in the reported negative background-subtracted signals, that the extraction with the relatively high number of negative values of background-subtracted signals may not be suitable for processing the current array. In general, this provides a user-friendly metric that enables a user to identify whether changes in hyb, wash and/or stripping procedures, or other array processing procedures or changes in a feature extraction parameter (e.g., background settings) have resulted in more (or less) negative signals (after background level subtraction) then what occurred previously before the change(s). If the number of negative features exceeds a given threshold, run summary 101 may show a warning. FIG. 1C show an example of such warning 107 stating: "WARNING: There are 579 (Green) negative features. Possible problem with background correction method selected".

Another plot 280 (FIG. 1B) that may be reported in QC report 100 is a signature plot, also referred to herein as an "M vs. A" plot, or magnitude vs. amplitude plot. Plot 280 plots log ratio values of the signals versus the average log signal value. The system plots only the log ratio and signal values of the non-control features that are inliers (i.e., neither non-uniform nor saturated). Additionally, the system may show outliers and/or controls in a separate plot. Log-ratios that are significantly up-regulated may be color-coded with a first color 282r (such as red in the example in FIG. 1B) and log-ratios that are significantly down-regulated may be color-coded with a second color 284g (such as green in the example in FIG. 1B). Log-ratios are determined to be significantly up-regulated or significantly down-regulated based on an error model provided with the feature extraction module of the system. The feature extraction software calculates a log-ratio error along with each log-ratio, and from this log-ratio error, calculates a p-value. If the p-value calculated is below a given threshold, e.g., 0.01, that log-ratio is then called "significant". The p-value threshold is user settable in the protocol.

Signals that were used for normalization of the plot may be color-coded in a third color 286b (such as blue in the example shown in FIG. 1B). Features that are in both classes, that is, their signals were used for normalization and their signals were determined to produce significant log-ratios as well, have precedence for color-coding for the significant log-ratio color (e.g., red or green). Feature with log-ratios that were neither significantly up- or down-regulated, nor had signal used for normalization, may be color-coded with a fourth color 288y (such as yellow in the example shown in FIG. 1B). The total number of significantly up-regulated and down-regulated signals may be numerically reported at 290 (for non-control inlier features).

The spatial distribution of the up-regulated and down-regulated features on the array may also be plotted as in plot 300. The signal values color-coded with colors 286b and 288y in plot 280 are not included in plot 300, only those non-control signals found to be significantly up-regulated 282r and significantly down-regulated 284g are shown in plot 300, to show the spatial locations of the features on the array that produced those significantly up-regulated and significantly down-regulated values. In one aspect, the signals are plotted corresponding to the row and column locations of the features on the array that produced the signals. Ideally, the red and green features should appear homogeneously mixed, or random, much like what is shown in plot 300. This plot can be very useful in identifying array processing problems or feature extraction algorithm problems, such as problems with de-trending. For example, if the upper right quadrant of plot 300 shows predominantly red signals and the lower left quadrant of plot 300 shows predominantly green signals, this will immediately alert an observer that there is a problem with the array results, and that that the problem may lie with hybridization, washing, stripping, and/or target preparation. These types of artifacts can also be seen by viewing the image with appropriate color-scale manipulation. In addition, the presence of gradients can point to a problem with the feature extraction algorithms; that is, if the spatial detrending algorithm was used, it may have underestimated the gradient. If the user did not choose to use the spatial detrending algorithm in the protocol, then these plots can alert the user to re-extract with the spatial detrending algorithm turned on. Accordingly, QC report 100 functions not only to alert a user when there is a quality problem with an array, but also may help to diagnose the source of a problem, and give the user one or more specific preparation and/or processing steps to look at as possible causes of the problem.

The metrics in QC report 100 that follow are summary statistics. That is, these statistics report averages, standard deviations, medians, etc. of a population of features. As discussed earlier, all summary statistics use at least the three following filters: one, the features considered must be inlier (neither non-uniform nor saturated) features; and two, the number of inlier features (per probe) has to be greater than or equal to a minimum replicate threshold (which may be indicated by the user in the protocol), and three, the summary statistics use features that are filtered for a given probe type. For example, spike-in summary statistics require that each feature considered must qualify as a spike-in probe (and user indication that spike-in target has been added).

QC report 100 may further include a numerical report 320 characterizing the signal reproducibility of non-control replicated probes. Again, the grid template of an array may provide information to the feature extraction module so that the system can filter the features to determine which are non-control probes. Furthermore, only inlier, non-control signals are reported on, since outliers (e.g., non-uniform and/or saturated outliers, as determined by techniques described above) tend to skew the % CV (coefficient of variation) values unrealistically. If a non-control probe has a minimum number of inliers, a % CV (percent coefficient of variation) of the background-corrected signal may be calculated for each channel (i.e., standard deviation of signals/average of signals). This calculation is done for each replicated probe, and the median of those % CV's is reported. A lower median % CV value indicates better reproducibility of signal across the microarray than a higher value. The median values for the population of % CV's are calculated and displayed for each channel (red 322r and green 324g in the example shown in FIG. 1B). This metric is useful to characterize reproducibility of signal across the array, for experimental types of probes.

QC Report 100 may display two metrics that measure the uniformity of replicated log ratios and that indicate the span of log ratios: absolute average log ratio, i.e., AbsAvgLogRatio, and average signal-to-noise, i.e., average S/N 346. These metrics are calculated from inlier features of replicated non-control and spike-in probes.

For example, some microarrays may have 100 different non-control probe sequences with 10 replicate features each. For each replicate probe, the average and standard deviation of the log ratios are calculated. The signal to noise (S/N) of the log ratio for each probe is calculated as the absolute of the average of the log ratios divided by the standard deviation of the log ratios. From the population of 100 S/N's, for example, the average S/N 346 is determined and shown in table 340. Spike-in replicates are processed similarly, and the average S/N 348 for Spike-in probes is also shown in table 340.

The AbsAvgLogRatio metric indicates the amount of differential expression (up-regulated or down-regulated). As described above, averages of log ratios are calculated for each replicated probe. The absolute of these averages is determined next. Then, the average of these absolute of averages is calculated to get a single value for the QC Report for non-control probes and spike-in probes, respectively, see 342 and 344 in FIG. 1B. The larger this value, the more differential expression is present.

Thus, table 340 characterizes array uniformity by reporting absolute average log ratios of replicates of non-control log ratios 342 and replicates of spike-in probe log ratios 344. By measuring the absolute values of the log ratio signals, an average value can be calculated for the non-control replicates and the spike-in replicates as a measure of an overall expressiveness of the array. Thus, for example, if the average of the significantly up-regulated, non-control signals is 0.21 and the average of the significantly down-regulated, non-control signals is −0.11, given an equal number of signals in each group, the overall average would be average would be 0.05. However, by taking the absolute value of each average and the calculating an overall average, the metric takes into account expressiveness in both directions (positive and negative) without negating one against the other in the calculation of an average, to give a better indicator of overall expressiveness, in this example, 0.16.

Additionally, reproducibility of the log ratios of replicate probes may be characterized by calculating an average signal to noise ratio (S/N) ratio for non-control probes and spike-in probes (346 and 348, respectively).

These values can be tracked across multiple arrays. Although threshold values may not necessarily be employed, a user can get a good idea of a range of S/N values that are typically seen. Further statistics can be calculated across multiple arrays to determine mean and standard deviation of the reported average S/N values typically observed. In this way, if a particular array is reported to have a non-control average S/N 346 and/or a spike-in average S/N 348 is significantly off from the previously calculated mean of these values across a plurality of arrays, then the user can be alerted that there is a problem with the present array. Further in this regard, users can customize the system by setting their own threshold levels, with regard to the report currently described and/or any other metrics reported in the QC report. Continuing with this example, the user may set thresholds based on the mean and standard deviations that were calculated across multiple arrays. Going forward, an array with results outside one or more of the threshold levels having been set would automatically be flagged at the metric exceeding the customized threshold.

Metrics that may be particularly useful for single channel array analysis include signal intensity values for identical sequence probes in different arrays, grid plots, outlier counts, goodness of fit metrics, foreground and multiplicative detrending metrics, median % CV's of replicated probes, and relative signal ratios amongst different spike-in probe sequences, as discussed herein.

The system does not determine the "sensitivity" of an array, since, as noted earlier, the term "sensitivity" is open to different interpretations and definitions by different users and manufacturers. However, the system does provide a sensitivity metric that can be tracked consistently over a plurality of arrays and compared between arrays. It is reproducible and can be tracked or followed to compare each array on a consistent basis. For example, metric 360 reports the ratio of net feature signal to net background used for the two dimmest spike-in probes on an array containing spike-in probes. For example, if there are ten spike-in probes present on an array, each with replicates, the calculations for metric 360 are performed on the two probes that are present in the lowest copy number in the spike-in target mixture (e.g., "r60_a97" and "r60_n11" in the example of FIG. 1B). Signal to Background Ratio (i.e., S2BGUsed) is calculated for each feature (e.g., by calculating net signal/net background used signal). If, for example, there are thirty feature replicates of "r60_a97", then the median S2BGUsed of those 30 S2BGUsed values is reported in QC report 100, and similar reporting is carried out for "r60_n11". Values for each channel are reported.

A plot 380 of the percentage coefficient of variation of the average background subtracted signals may also be provided for each spike-in probe to provide the user with a graphical representation of the performance of the signal reproducibility of the replicates. As described above for non-control probes, % CV's are calculated for inliers for both red and green background-corrected signals. The % CV for each probe is plotted vs. the average of its background-corrected signal. The medians 382 of this population of % CV's may be calculated and numerically displayed with respect to each channel.

Spike-in log ratio statistics may also be reported in table 400. By definition, spike-in probes will have an expected log ratio signal value, which is reported at 404, adjacent each respective probe name 402. The actually observed average log ratio values of the replicate log ratio values are reported at 406, with the standard deviations of the same reported at 408. The S/N values 410 are calculated by dividing the absolute value of value 406 by value 408, for each respective set of replicate probes.

The expected log ratio values 404 for each set of replicate spike-in probes may be plotted against the observed average expression value, respectively, in plot 420. By generating a best fit line 422 to the plotted values, the slope 424 and Y-intercept 426 can be determined. An $R^2$ term 428, sometimes referred to as a coefficient of determination, can also be calculated to indicate the correlation of the line fit between the observed and the expected log ratio values. A linear regression analysis is done using the plotted values to generate the best fit line 422. A slope of 1, y-intercept of 0 and $R^2$ value of 1 is the ideal of such a linear regression. A slope<1 may indicate compression, such as having under-corrected for background, or if the wash stringency is too low. The regression coefficient of determination ($R^2$) reflects reproducibility.

That is, the closer that the slope of line 422 is to 1, the closer are the observed values to the expected values. The Y-intercept value should ideally be at zero, and deviance from zero indicates some bias towards one channel or the other, depending upon whether the Y-intercept value 426 is positive or negative. $R^2$ values are also ideal as a value of one, with lower values indicating noise in the system.

In addition, or alternative to the graphical metric 120 one or more other "goodness of fit" metrics may be calculated and displayed to indicate problems with the initial fit of the grid of the feature extraction module to the features on an array and/or with respect to the accuracy of the spot finding algorithm of the feature extraction module. Like other metrics described herein, a goodness of fit metric provides a metric that may be consistently applied across multiple arrays, allowing a user to track results to compare and contrast arrays results, including the ability to customize one or more threshold levels that the system may use to automatically determine a "good fit" versus a "bad fit".

Figure 4:
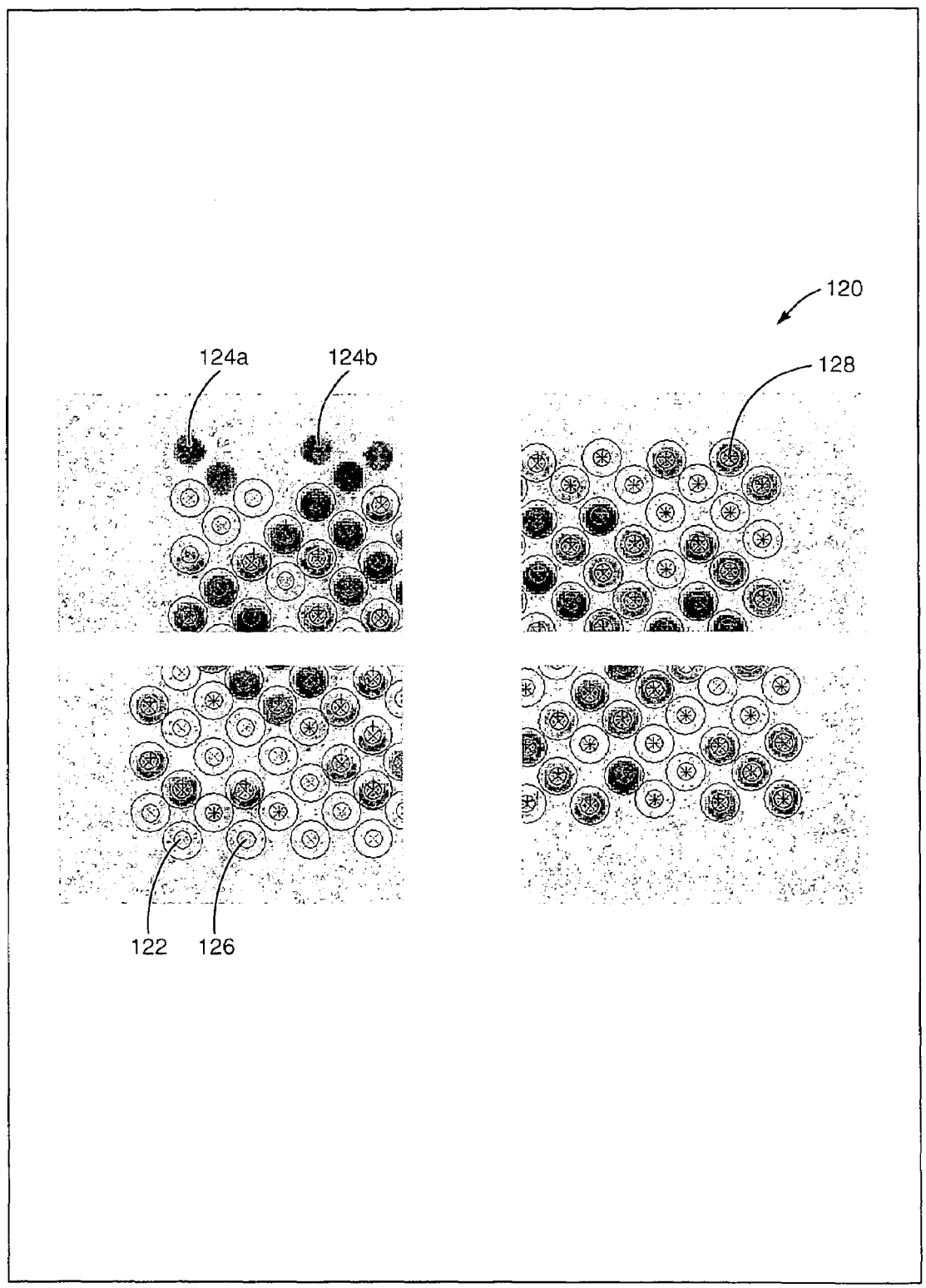
FIG. 4 is shows an example of a graphical metric indicative of accuracy of location of features by a feature extraction process used to extract signals from features of the chemical array.

Referring to FIG. 4, another example of a graphical goodness of fit metric 120 of the type previously described above with regard to FIG. 1A is shown. As can be seen from the above shape file, the image was gridded incorrectly, especially on the left side, as can immediately apparent from features 124a and 124b that have no centroids 122 associated therewith. Also, examples of centroids 122 are readily apparent that are placed on background, nowhere near a feature 124 (the same is true of the cookie shape 126 which has been displayed in this example). As noted above, this metric displays only portions of the array, e.g., only the four corners, each typically with about twenty±ten features 124 (although this metric is not limited to this number of features per corner, as more or fewer features may be displayed). The pixel values (i.e., x=column position, y=row position) of the feature positions may be taken directly from the image, in order to detect if there has been a rotation of the array. In this example, for the first and last features 124b and 128, respectively, of the first array row, the pixel column positions were eighty-five and sixty-five, respectively, indicating a very large rotation of the image (about twenty pixels).

Numerical Goodness of Fit Metrics

In addition to the graphical goodness of fit metrics, the system may also calculate numeric values that indicate the goodness of fit. As discussed above, goodness of fit metrics can find problems with the manner that the feature extraction software finds and places a grid over the array. However, these metrics may also flag an array that actually has features in a non-systematic placement on the array, as may occur with some types of synthesis problems (e.g., head positioning problems), and/or the metrics may flag an array that has large areas of population and/or non-uniform outliers, due to target preparation, hybridization and/or wash problems.

One goodness of fit metric that is applicable in this example has already been described earlier with regard to reporting on the individual features, i.e., the system may sum the number of non-uniform and population outliers as described with respect to metric 180 above. Table 1 below compares the numbers of outliers for features and background that were summed for the mismatched gridding in FIG. 4 versus the numbers of outliers for features and background of the same array when the grid was properly aligned. The outliers have been summed for features or local backgrounds that were flagged in red or green channels.

TABLE 1

Comparison of Outliers - Wrong Grid vs. Correct Grid

|  | Wrong Grid | Correct Grid |
|---|---|---|
| FeatureNonUnifOl: | 2.5% | 0.0023% |
| BkgdNonUnifOl: | 18.2% | 0.0023% |
| BkgdPopnOl: | 32.1% | 1.79% |

As expected, the number of outliers flagged with the wrong grid is much larger than for the correct grid. This metric can be made more sensitive and specific by summing and calculating a percentage of a subset of the outliers on the array: for instance, only those features and local background regions that are in the first or last rows or first or last columns of the arrays may be summed and calculated. A threshold may be determined for this metric. For example, an array with a percentage of non-uniform features over such a threshold may prompt an error message 103b in run summary 101 (see FIG. 1C) such as: "ERROR: The grid may be placed incorrectly. There are a large number of non-uniform or not found features along the array edges". Other goodness of fit metrics, such as position and signal metrics, may be used in concert with the outliers metrics to specifically identify grid problems, as described below.

A goodness of fit metric referred to as a delta metric herein may be used in identifying gridding problems. The grid file associated with the feature extraction process for an array being processed identifies the positions for each feature 124 for both the original nominal grid (GridX and GridY) and, the final spot calculated position used to identify and extract the feature 124 (SpotX and SpotY). In one aspect, to calculate a delta metric, the system compares these pairs of positions for each feature, to provide a delta metric for each feature. The delta metric may be defined by:

Delta metric $Y$=Absolute value of $\{SpotY-GridY\}$ and

Delta metric $X$=Absolute value of $\{SpotX-GridX\}$.

These deltas ("AbsDiff") correspond to the difference between the spot and grid position in the array rows and columns, respectively. If a particular feature fails a feature extraction test referred to as "IsFound", this indicates that the feature extraction software was not able to confidently locate or "find" the feature amongst the background signal. Thus, the features that were not successfully located by feature extraction (e.g., as identified by failing the "IsFound" test) are omitted from the delta metric (AbsDiff) calculations. The Delta metric Y values may be plotted against the Delta metric X values with respect to each feature considered (not shown). Table 2 shows results of averaging the Delta metric X values (columns) and Delta metric Y values (rows values) across all features considered.

TABLE 2

Average of Absolute Difference (Spot-Grid)
Average of Absolute Differences (Spot-Grid):

| FE Grid: | "X" (Columns) | "Y" (Rows") |
|---|---|---|
| Correct | 2.50 | 5.72 |
| Wrong | 2.54 | 12.5 |

It is readily apparent that the averaged values of the Delta Y metric are much greater for the example where the grid was applied incorrectly than for when the grid was applied correctly, accounting for that twenty-pixel disparity that was discussed above. The Delta X metrics, on the other hand, are fairly close to one another, indicating that the columns were aligned pretty well even in the instance where the grid was rotated ("Wrong"). The delta metric is robust to different array types and different targets. A threshold may be determined for this metric, such that an array with an average AbsDiff_X or AbsDiff_Y that exceeds such threshold will prompt an error message 103a in run summary 101 (FIG. 1C) such as "ERROR: The grid may be placed incorrectly. The spot centroids are shifted relative to their nominal grid".

However, the average AbsDiff metric are only useful for grid and/or spot-finding errors if the error is a fractional amount of the distance between features. For example, if the grid were shifted over to the right by exactly the distance between columns, then the grid would align correctly with the features, but would just miss the first column of features altogether. The first column of features would be ignored as failing the IsFound test, and the remaining features would show no disparities by calculating delta metrics. In such an instance, other goodness of fit metrics may need to be employed.

For example, another goodness of fit metric summarizes the percentage of features that fail the "IsFound" test. For more sensitivity and specificity, this metric may be narrowed to include only features from the first and last rows and from the first and last columns. Often in case of a grid failure, a grid is shifted by one column spacing in the left or right or the grid may be shifted up or down by a row spacing. To capture this failure mode easily, the number of non-uniform and not found features may be counted in the first and last rows or columns. A threshold may be determined for this metric. For example, an array with a percentage of not found features that exceeds a given threshold may prompt an error message 103b in run summary 101 (FIG. 1C) such as "ERROR: The grid may be placed incorrectly. There are a large number of non-uniform or not found features along the array edges".

For example another goodness of fit metric relies upon net signal statistics between different sets of probe types. If the grid and/or spot finding algorithms of the feature extraction process are incorrect, then the signals for a particular feature and background may be contaminated by other signals from other features. Similarly a signal for background may be contaminated by signals from other features, and a feature signal may be contaminated by signals from the surrounding background regions. This metric is generated by calculating the net signal (i.e., NetSignal) of the feature (e.g., mean signal minus scanner offset, as described above). This calculation may be done for various types of probes, for example, for all negative controls probes (control type=−1), all non-control experimental probes (control type=0), or all positive controls probes (control type=+1) on the array. The average net signal may be calculated for each probe type. Table 3 shows results of averaging the net signals for every feature on the array for each channel (red=rNet, green=gNet) with respect to the three control types. This was done for an array that has been correctly gridded (correct) and for the same array that has been incorrectly gridded (wrong).

TABLE 3

NetSignal Calculations

| ControlType | Grid | rNet | gNet | count |
|---|---|---|---|---|
| −1 | correct | 21.2 | 12.5 | 314 |
| −1 | wrong | 172.3 | 55.6 | 314 |
| 0 | correct | 441.7 | 109.6 | 41675 |
| 0 | wrong | 346.3 | 91.1 | 41675 |
| 1 | correct | 1955.9 | 949.6 | 1942 |
| 1 | wrong | 1159.8 | 554.0 | 1942 |

For both positive controls and negative controls, it is readily apparent that the NetSignal values for both red and green channels are significantly different for the incorrectly gridded example as compared to the correctly gridded sample. Thus, by tracking these metrics, a user may generate typical threshold values that are expected. Alternatively, even if customized threshold values are not calculated, a user will typically know the ballpark numbers that are expected from these metrics after running multiple numbers of arrays that are correctly gridded, so that spotting an incorrect gridding will be generally apparent when viewing the metrics for the same. Still further, a comparison of these metrics across a plurality of arrays will allow even a novice user to readily visually identify when there has been a gridding error. For example, in Table 3, the contamination of features is especially evident with the negative controls group (i.e., much higher signal is associated with the wrong grid, due to contamination by features that are not actually negative controls, than the correct grid). The signals of the positive controls group, however, are also decreased by the incorrect grid, as expected, due to contamination by weaker features and/or local background regions, and as is readily apparent by reviewing Table 3.

For example, another goodness of fit metric relies upon signal to background levels (S2Bkg) and rations of these S2Bkg levels between different sets of control types. This metric is generated by calculating the NetSignal of each feature (e.g., MeanSignal—scanner offset) and dividing it by its NetLocalBackground signal (e.g., BGMeanSignal—scanner offset). This is done for all features within a given type of probes; for example, for all negative control probes or all spike-in probes on the array. The average of the signal to background ratios ("AvgSig2Bkg") is then calculated across all features for each control type. Table 4 shows the results of such calculation for the same example that has been discussed immediately above.

TABLE 4

AVERAGE SIGNAL TO BACKGROUND RATIOS

| ControlType | Grid | rS2bkg | gS2bkg | count |
|---|---|---|---|---|
| −1 | correct | 1.1 | 1.7 | 314 |
| −1 | wrong | 8.1 | 7.0 | 314 |
| 0 | correct | 22.5 | 14.5 | 41675 |
| 0 | wrong | 16.1 | 10.9 | 41675 |
| 1 | correct | 96.1 | 124.2 | 1942 |
| 1 | wrong | 54.5 | 67.3 | 1942 |

It can be readily observed upon reviewing the signal to background ratios metric in Table 4 that for negative controls, the average signal to background ratio is increased by the contamination of brighter features when the wrong grid is used. Similarly, with regard to positive controls, the average signal to background ratio is decreased by the contamination of weaker features and by background regions when the wrong grid is used. The signal to background ratios metric is more robust to different target types than the simpler NetSignal metric discussed above. A more sensitive and specific variation of this metric is achieved by calculating the AvgS2Bkg for a subset of the positive controls (e.g., a specific type of spike-in controls if they are present on the array and if the spike-in target is present). These metrics (i.e., average signal to background) for the negative controls and for the spike-in controls can then be used in the statistics table output to track metrics for negative controls and spike-ins, respectively, over time and/or over a series of arrays.

These NetSignal and Signal to Background metrics can be used to detect grid and spot finding problems when a user tracks many arrays that are using similar targets, as noted. However, a metric that is more robust in evaluating different target types involves the calculation of the average signal to background ratio for the above control types, and then dividing the AvgS2Bkg of the one type of probe by the AvgS2Bkg of a different type of probe. For example, a ratio may be calculated between the average signal to background ratio for positive controls and the average signal to background ratio for negative controls (referred to as "PC2NC"). Table 5 shows the results of PC2NC calculations.

TABLE 5

AVERAGE S2Bkg RATIOS BETWEEN CONTROL TYPES

| Grid | rPC2NC | gPC2NC |
|---|---|---|
| correct | 86.8 | 74.1 |
| wrong | 6.7 | 9.6 |

As expected, the correctly gridded array has a lower S2Bkg for negative controls and a higher S2Bkg for positive controls. Thus, the correctly gridded array has a much higher PC2NC ratio of signal to background ratios, as compared to the incorrectly gridded array. The above analysis was done grouping all ControlType=1 (positive controls) probes together. For this array, there were many ControlType_1 probes that had no signal. Depending upon the array having spike-in (e.g., E1a) probes and the user having applied spike-in target(s) to the array, a more refined metric may result from using only the spike-in subset of positive controls probes. A subset of spike-in probes were chosen based upon those having a copy number of greater than or equal to three (thereby excluding three of the ten probe sequences, for example). The NetSignals were calculated as above and the average spike-in backgrounds were determined for each channel (AvgS2Bkg). Then the ratio of the average spike-in signal to background ("AvgSig2BkgE1A") to the average negative control signal to background ("AvgSig2BkgNegCtrl") was calculated ("E1a2NC"). The results are shown in Table 6.

The results from calculating spike-in signal to background ratio values and determining their ratio versus negative controls signal to background ratios, as described and shown in Table 6 are potentially more differentiating and robust than the results from calculating signal to background ratio metrics using all positive control probes as described above, and more robust than examining the S2Bkg for a single type of control probe set. That is, the average spike-in signal to background level ("avg_E1a2Bkg") is much higher when using correct gridding than it is when gridding is incorrect, as evident from reviewing the results of Table 6. Since the average signal to background for negative control is incorrectly higher for the wrong grid vs. the correct grid, this yields a much higher E1a2NC for the correct grid vs. the wrong grid. This metric can be reported in the statistics table output as "RatioSig2BkgE1a_NegCtrl". Finally, dividing the E1a2NC for the correct grid by the wrong grid ("Correct2Wrong") shows the span of this metric (for this one array) in differentiating a poor grid from a good grid (i.e. ~14-fold or 8-fold difference, respectively, for red and green channels).

TABLE 6

AVERAGE SPIKE-IN S2BKG RATIOS AND COMPARISON TO NEGATIVE CONTROLS S2BKG

| | avg_E1a2Bkg: | | avg_E1a2NC: | | Correct2Wrong | |
|---|---|---|---|---|---|---|
| Grid | Red | Green | Red | Green | Red | Green |
| correct | 654 | 601 | 591 | 358 | 13.9 | 8.0 |
| wrong | 345 | 313 | 42 | 45 | | |

Other goodness of fit metrics may examine the placement of the features with respect to the entire array image. This may result in determining that the scan was in error, that is, either the slide on which the array was deposited, was positioned incorrectly in the scanner, or the scanned image was cropped incorrectly causing a portion of the array to be outside of the image analyzed by the feature extraction module. Such an error may generate an error message in the run summary, e.g., "ERROR: Execution error: Grid is placed outside the scan!".

The header 440 of QC report 100 provides a readily available visual identification of the array and properties of the extraction of the array being reported upon, which may include the date 442 (e.g., date that extraction was performed and QC report 100 was generated) and a time stamp, identification of the array image 444, such as by file name or the like, feature extraction protocol (which determines which set of feature extraction parameters were used for the extraction) 446, User that performed the extraction 448, feature extraction module or software 450 used, grid 452 used. In addition, a subset of the feature extraction parameters may be shown, such as background correction method 454 used (or an indication that no background method was used, such as in the example shown in FIG. 1A), whether or not spatial de-trending 456 was used, whether or not a global background adjust algorithm 458 was used, and the type of dye normalization correction method used 460. Further additionally, a subset of the metrics from statistics table 500 (FIG. 5) may be shown, e.g., Linear Dye-Normalization Factors 462 used and Additive Error values used 464.

The information that is displayed in header 440 may be selected and customized by the user to display the information that the user finds valuable. For example, if the user always uses the same design file, protocol and grid, the user may choose not to display protocol 446, feature extraction 450 and grid 452 information in the header, but may decide to add hyb-wash information to be displayed. However, header 400 will initially contain a default format, such as the one displayed in FIG. 1A and the user can then modify/customize the header to display the information that the user is interested in. Other examples of information that may be displayed include the name of the laboratory that the experiments originated from, the name of the supervisor responsible for the data, a particular variable that the experiments are designed to explore, etc.

In certain aspects, the information can be used to establish an audit trail, for example, to establish that a QC protocol followed certain accepted or required standards (e.g., such as required by Federal regulatory standards) and to document any changes to such a protocol. In certain other aspects, only an approved user of the system may make changes to the information that is displayed (e.g., by providing password-limited access or other authorization feature that limits use of the system, for making modifications to the information, to such authorized users).

Figures 5, 6:
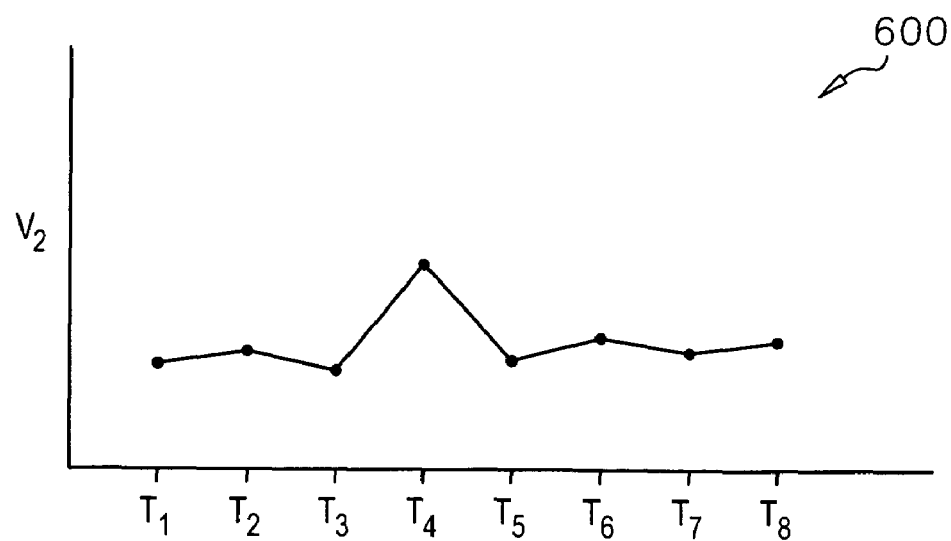
FIG. 5 is a schematic representation of a statistics table generated as described herein.
FIG. 6 is a schematic representation of a run chart or time series plot of values $V_2$ outputted by metric $M_2$ plotted over multiple time intervals, the values having been supplied from multiple tables.

As noted earlier, all numeric metrics displayed in QC report 100, and additional metrics not displayed in QC report 100 may be calculated and contained in a larger table (such as a statistics table, also referred to as "Stats table", for example) in addition to the textual output containing raw feature extraction measurements that is accessible by the system. The Stats table information can be present in the same file as the raw feature extraction data, or can be outputted as a separate text file, and a file saving option may be a user-settable parameter in the protocol. Referring to FIG. 5, a schematic representation of statistics table 500 is shown. Table 500 contains a large number of metrics 502, with metric names being contained in row 502, with the corresponding output values 504 being contained in the row 504 of statistics table 500. For example, Table 500 may contain metrics numbering in the neighborhood of one hundred or so, although, of course this number could be higher or lower. A relatively small subset of the metrics 502 are displayed in QC report 100 as were described above.

Figure 1D:
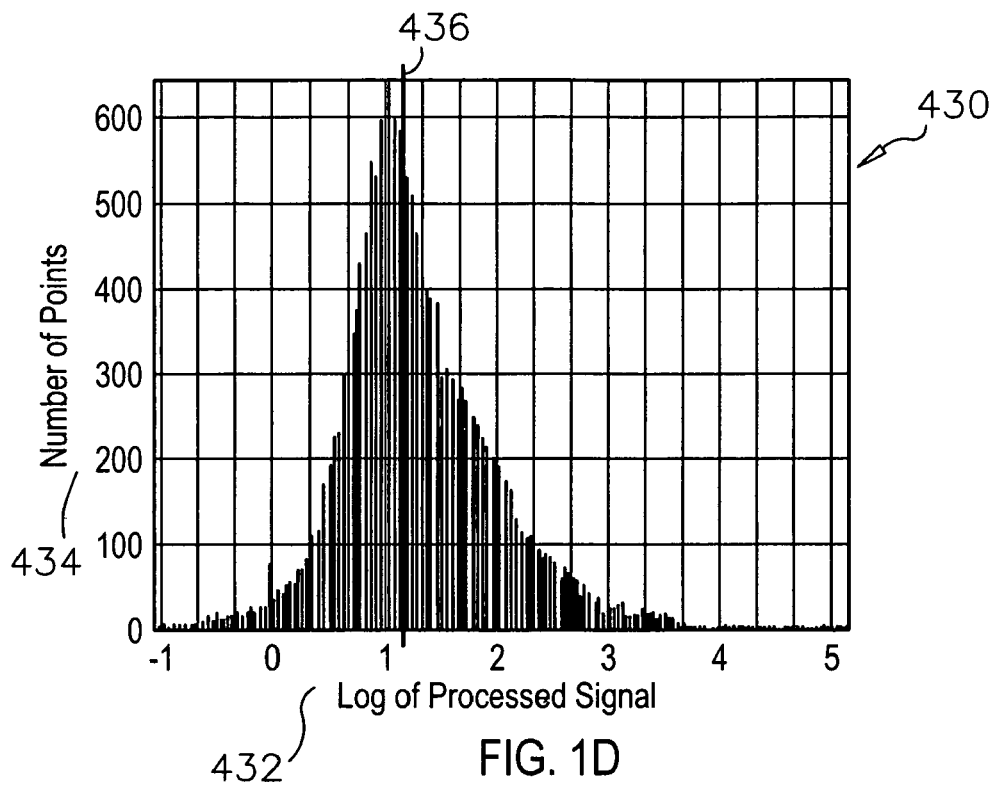
FIG. 1D shows an example of a histogram plotted to show the distribution of signals from a single-channel analysis.
Figure 1E:
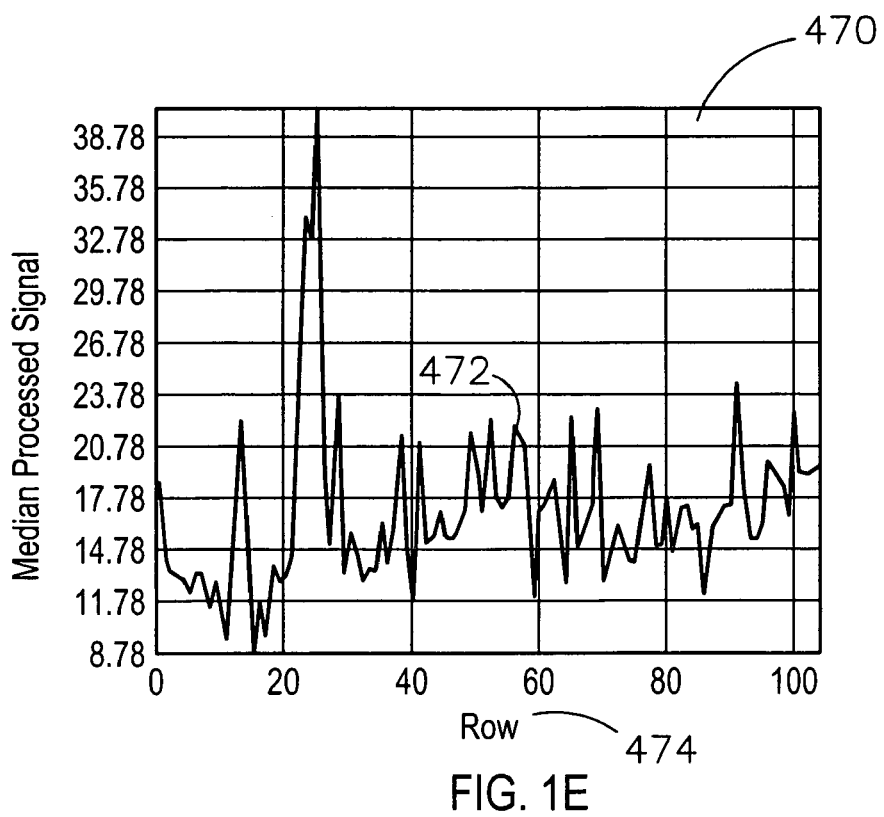
FIGS. 1E-1F show plots of median processed signals per row across all columns of an array, and per column across all rows of the array, respectively.
Figure 1F:
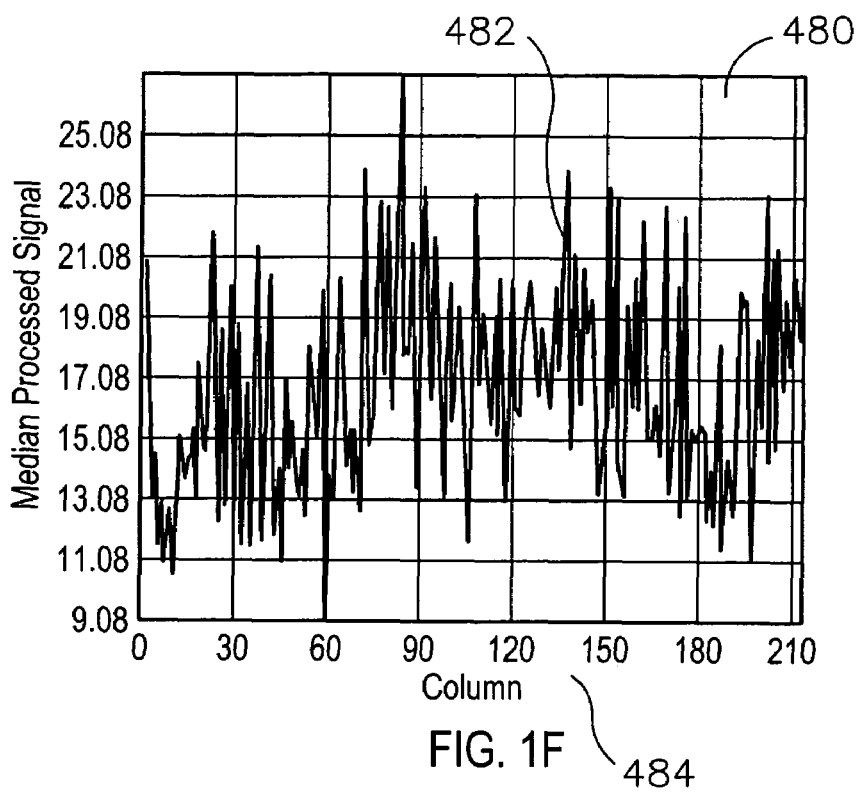

For single-channel and CGH data analysis, a slightly modified set of metrics may be calculated for table 500, and graphical metrics may be plotted in QC Report 100, as described herein. For single-channel analysis, a histogram 430 (e.g., see FIG. 1D) of signals may be generated to show the level of signal from the array and the shape of the signal distribution, wherein the log of the processed signals are plotted along the X-axis 432 and the number of points in each bin or bar of the histogram 430 are plotted against the Y-axis 434. The distribution of log (base 10) of the net signal (means signal minus scanner offset) may be plotted. For example, the X-axis of the histogram may range from −1 to five, and a fixed number of intensity bins may be defined in which each signal data point is contained. The Y-axis 434 scales so that the maximum data point (signal value) is in the bin with the most data points and the minimum data point is at zero. A line 436 at the median value with a net signal value may also be displayed at the median of the plot. Filtering may be applied so that only those signal values from features of control type zero that are not feature non-uniformity outliers are plotted. Additionally or alternative to displaying the median value line on plot 430, a plot 470 of the median processed signal 472, 482, respectively, per row 474 of the array 470 across all columns and/or per column 484 of the array 480 across all rows may be displayed, as exemplified in FIGS. 1E and 1F, respectively.

Another metric for single-channel analysis is referred to as Multiplicative Surface Fit, wherein it is determined to find the shape of the hybridization dome (i.e., the surface that fits over the values on the array). The RMS (root mean squared) value of the surface that is fitted through the log of all signal values, after filtering, is calculated. Filtering is performed to remove signals from probes having values below the noise level and probes that are not control type zero.

Another single channel metric is called the "Spatial Distribution of Median Signals for Each Row and Column", and is calculated to show any spatial trends remaining in the processed signal. A plot of signal versus row 470 is made to show the median processed signal 472 for each row over all columns. Likewise a second data set may be plotted on the same plot or different plot 480 to show the median processed signal 482 for each column across all rows. Filtering for this metric may be performed to remove from consideration all probes that are not control type zero or are saturated or feature non-uniformity outliers.

Figure 1G:
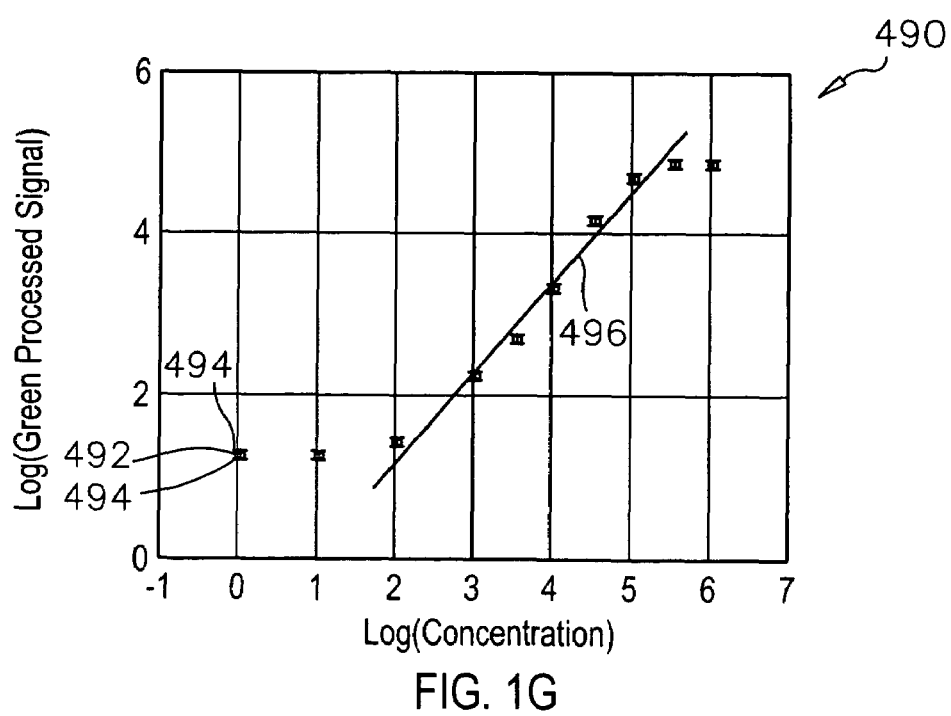
FIG. 1G shows an example of a spike-in plot.

A still further metric that may be calculated for single-channel analysis is a "Spike In Plot". A log-log plot of the signal of the spike-in probes versus the relative concentration (on an arbitrary scale) of the spike-in probes is made. FIG. 1G shows an example of a spike-in plot 490 in which log values of signals from one channel (e.g., green channel) of a two-channel analysis have been plotted against log value of the concentration values associated with the respective spike-in probes reported on. The scale of the x-axis is typically always the same, covering about six orders of magnitude, so that users can easily see shifts in the signal for a given concentration from one array to the next. For each sequence the median of the replicate features is displayed as a data point 492 and the standard deviation of the replicates may be displayed as an error bar 494 through the data point 492. A line fit 496 may then be plotted through the data points 492 that fall on a linear portion of the curve defined by the data points 492. The fit is accomplished in log space and the data points 492 may be weighted based on the inverse of the error bar values. The fitted line 496 typically extends from the minimum to the maximum point determined to fall in the linear region. An associated table may be outputted to show the minimum and maximum relative concentration of the linear range, the average of the medial signal levels of those sequences that are dimmer than the linear region, the average of the standard deviations of those probes that are dimmer than the linear region, and the slope (in linear space) of the line fit. Filtering of the data, prior to performing calculations for this metric, may be performed so that only spike-in probes that are not feature non-uniformity outliers are considered.

For CGH array analysis a metric for derivative of log ratio signals may be calculated and outputted in the statistics table 500 for those arrays that indicate a CGH-type array in the protocol. By calculation of the derivative of the log ratio signals, a robust estimate of noise is provided. The spread of the log ratio differences between consecutive probes along all chromosomes represented by the CGH array is calculated and divided by the square root of 2 to counteract the effect of noise averaging. The probe signals from the array are first rearranged to correlate to their positions represented on the chromosomes, thereby mapping them to the chromosome locations (chromosomal coordinates represented by each probe, respectively), with log ratio values of the two channels for each location/probe represented by data points (signal levels read from probes). Where the genetic material is "normal" and no amplification or deletion has been reported, the average log ratio signal is about zero, as expected, since the fold number should be the same in both channels. When one channel represents abnormal tissue, such as cancer tissue, for example, and the other channel is a control channel representing normal or non-cancerous tissue, then the regions in which amplification or deletion has occurred in the cancerous or otherwise abnormal tissue shows up by log ratio values that deviate from zero, e.g., a value around +1 for an amplification of two, or a significantly negative value indicating a deletion. The amount of the negative value plotted depends on the average ploidy of the sample and the copy number of the deletion or amplification. For example, if the average ploidy is two, a 1:2 deletion will show a log ratio of about −0.7 to about −1.0. As another example, where the average ploidy is two, a 3:2 amplification will show a log ratio of about 0.4 to about 0.6.

The derivative values are calculated by $DLR_i = LR_i - LR_{i-1}$, where DLRi is the derivative of the log ratio value at log ratio data point i, $LR_i$ is the log ratio value data point i and $LR_{i-1}$ is the i-1$^{st}$ log ratio data point, and i ranges from one to the total number of data points. The derivative values DLR are all around zero value on average, except for values that initially jump or drop to begin or end the indication of an amplification or deletion. An inter-quartile range of the DLR value may be determined (e.g., by ranking the DLR values from lowest to highest or highest to lowest, and then considering only those data points from the twenty-fifth percentile to the seventy-fifth percentile of the ranked range), to eliminate the outlier values, including those defining the spikes where the jumps and drops occur.

The DLR values in the inter-quartile range, referred to as DIQR are then mathematically converted according to the following formula to provide the spread of the derivative of log ratio values: Spread=(dIQR/erfinv(0.5)*2*$\sqrt{2}\sqrt{2}$). The extra $\sqrt{2}$ division is needed to convert from derivative log ratio space to log ratio space, and erfinv(0.5)*2*$\sqrt{2}$ is a constant that compensates for use of the inter-quartile range as opposed to the entire range, based upon a normal distribution, where "erfinv" represents and inverse error function. Thus the spread of the derivative of log ratio values is determined as a measure of noise characterizing the array.

Just as header 440 may be customized by a user to display information that suits the user's needs, the body of QC report is also user-customizable, so that particular graphical metrics as well as numeric metrics may be selected by the user to display those metrics best suited for the user's particular needs for a project. A user may save such customization preferences as a template and have different templates for different types of array platforms (e.g., CGH, Location Analysis, single-channel microarrays, etc.) as well as different needs that may be imposed by a particular project that may depend upon the focus of the project (e.g., quality control, the need to look at particular types of probes, parameter tuning of software, or particular types of measurements that are considered most critical to a particular project). In addition to viewing QC report 100 for a quick and easy reference indicating the quality of an array, a user may additionally access Table 500 to view the numeric metrics displayed in QC report 100, and to view additional metrics for a more in depth study of any particular array as desired.

Further, Table 500 may be used for tracking, such as to produce a run chart, for example. In this regard, a user may append multiple tables 500 to an additional table, such as by using Microsoft Excel® or Microsoft Access®, for example, to generate a time series of these metrics (e.g., such as a time series of a particular metric). Any one or more of metrics $M_1$-$M_N$ can then be plotted over time to study changes in the metric values, by plotting the values for a particular metric from each of the times stored by each Table 500 in the series of tables having been assembled as described. FIG. 6 is a schematic representation of a run chart or time series plot of values $V_2$ outputted by metric $M_2$ plotted over eight time intervals, the values having been supplied from eight Tables 500. It is readily apparent from reviewing chart 600 that the value $V_2$ outputted by metric $M_2$ at time $T_4$ appears to be anomalous with regard to the other values plotted. For example, the metric may be one of the goodness of fit metrics described above, where a user can track how well the feature extraction module fitted the grid to the array and located the features prior to extracting signals. A run chart of this data would help to identify an acceptable range of metrics for which goodness of fit would be considered to give the best results for signals extracted from an array, and may also specifically identify those arrays that would be considered least reliable. In this sense, the run chart does not necessarily have to be a time-series study, but may alternatively be a study of a series of arrays, from the same experiment, that were extracted together in a batch mode, for example. Other groups of arrays may be those having the same target, those from the same type of platform (gene expression, CGH, Single Channel, Location Analysis, etc.), those comparing different wash protocols, etc. Note that this is just a simple example, and that a typical time series may contain hundreds or thousands of data points obtained from hundreds or thousands of Tables 500. The set of arrays that are to be used in such run charts may also be customized. For example, by using information from the feature extraction parameters, such as array design, user name, etc., a user can select just those data sets (arrays) that are appropriate for a desired run chart. Information from a user such as sample type, wash conditions, etc., can also be provided by the user to the feature extraction software used to perform the extraction of the arrays and such information may be stored with the array results in a database.

In certain aspects, the system does not preset thresholds and such run charts may be used to generate customized thresholds set by a particular user, for a particular type of array, run conditions and experiment, for example.

Further examples of metrics that may be calculated and outputted by the system in statistics table 500 and/or QC report 100 are described below. It is noted that these are only meant to be examples of further metrics that the system may be configured to calculate and output and that the system is not limited to these and the above specific metrics, as other quality metrics may be calculated and outputted, such as others known to those of skill in the art and equivalents thereof, etc.

In another aspect, the system further comprises "Image View" capabilities, providing an image of the entire array, showing all features as displayed for visual inspection ("visual QC") by a user. The image may be in false color, such as a two-channel false color image of the array, for example. For batch processing, this viewing may be somewhat more tedious in the workflow, as noted above. The image may be auto-scaled (unless changed by user), such that the color scale spans the 1% to 99% signal ranges. This color scale may or may not be the correct scale to show array synthesis or hyb/wash artifacts.

Find Spots—Spot (Feature) Size Summary metric—This metric is designed to assist in identifying problems such as array synthesis problems. Summary statistics that may be reported in this metric may include, but are not limited to, maximum spot (feature) size, $99^{th}$ Percentile ("99%") size, median size, standard deviation of feature size, first (1%) percentile feature size and minimum feature size.

Find Spots—Summary of Number of IsFound features for each channel: This metric indicates the number of found or "strong", features. A low number may indicate a problem with the feature extraction spot finding algorithm.

Feature Pixel Outlier analysis (for each channel)—The number of low and high pixel outliers that are omitted from features can be used to detect array synthesis flaws, as well as other array processing artifacts (e.g., such as hyb, wash and/or stripping artifacts). The feature extraction module outputs the number of low and high pixel outliers detected and removed for each feature. The QC metric generated shows show summary statistics (i.e. across all features on array) for these numbers: maximum (i.e., maximum outlier value), ninety-ninth (99%) percentile, and median values for numbers of pixel outliers detected and removed.

Raw signals of features—the indication of the signal range on an array, for different classes of probes may be interpreted as a measure of dynamic range of those signals.

Summary statistics—Number of Saturated Features— outputs the number of saturated features that were identified.

Statistical summary of Feature Net signals—In order to be independent of the scanner version, this signal will be "Net" signal, that is, after scanner offset subtraction. Net signal statistics indicate the dynamic range of the signal on a microarray for both non-control probes and spike-in probes. The QC Report 100 may use the range from the 1st percentile to the 99th percentile of the population of net signals for each channel as an indicator of dynamic range for that microarray. May also include median value. Alternatively, the signal information may be plotted as a histogram.

The above summary statistics may be summarized across all probe sequences for two classes of probes: non-control probes (i.e. ControlType=0), and Spike-in probes (i.e. subgroup of ControlType=+1)

Negative Control Net signal summary statistics—outputs the number of inliers (i.e., signals from those negative control probes, the features of which are neither non-uniform nor saturated. Average signal values and standard deviation are reported.

Statistical summary of inlier background net signals: in addition to metric 220 described above, median, skew, and inter-quartile range (IQR, to indicate spread) may also be calculated and outputted to characterized inlier background net signal distributions. In order to be independent of the scanner version, this signal will be "Net" signal, that is, after scanner offset subtraction. Non-uniform and population outliers are omitted. Statistics may be summarized for the following types of backgrounds: local background regions, negative control probes (control type=−1), and Spike-In probes (if their respective targets are not present in the hybridization). Alternatively, the signal information may be plotted as a histogram.

Plot of Local Background Net Signals—This metric shows a histogram of the net signals of local background regions (e.g., in two colors to indicate red and green channels, for a two-channel array). This visual tool may be useful in monitoring and identifying hyb/wash problems.

Spatial Detrend Summary (for each channel)—The Spatial Detrend algorithm attempts to account for low signal background that is present on the features and varies across the array. A relatively high value reported (i.e., relative high RMS_Fit number) can indicate gradients in the low signal range before detrending. A metric ("RMS_Resid") may also be reported to indicated the amount of residual noise after detrending. An average fit value ("AvgFit") indicates how much signal is in the "foreground". A higher AvgFit number indicates a larger amount of signal was detected by the detrend algorithm and removed.

Background Subtraction of Feature Extraction Parameters—the metric summarizes background parameters set by user (and are also in the feature extraction text output; but may be repeated in the QC Report 100, such as in the header, for example, to aid users in comparing different background methods). Parameters include settings for the initial background algorithm used (e.g. No Bkgd; LocalBkgd; NegControls; etc.), whether Spatial Detrending is on or off, and whether Global Background adjustment algorithm is on or off.

Background—Used Summary Statistics—this metric may aid the user in assessing the average background calculated for an array, dependent upon which feature extraction methods are chosen for feature extraction processing. These statistics may indicate scanner offset values, initial background algorithm used, spatial detrending surface used, and global background adjustment for each feature. Averages over all features may be reported.

Background-Subtracted Signal Summary—Negative Control Inliers—this metric summarizes the signals from the negative control inliers after background subtraction. An average signal and standard deviation may be calculated in this regard. The average signal indicates where this population of probes lies in the post-background-subtracted signal space. The standard deviation of the signal is useful for understanding the noise at the low end of the signal range. It may also be useful to compare different background-subtraction methods. For example, if a first background method (background method 1) is chosen (such as No Background, or a global type of background correction method, for example) and if a second background method (background method 2) is chosen (such as the Local Background method, for example), these two extractions can be compared in the following manner. If a background method has been useful, generally the observation will be that the standard deviation of the negative controls determined with background-subtracted signals (SD_BkSub) will be less than the standard deviation of the negative controls determined with NetSignals (SD_Net). Further, if in the above example, the SD_BkSub_2 (i.e., SD_BkSub value calculated using background method 2) is less than the SD_BkSub_1 (i.e., SD_BkSub value calculated using background method 1), then this indicates that the Local Background method was better for this array than using no background or a global type of background method. Generally, the Local Background method is appropriate if there is a correlation between signals of local backgrounds and signals of features (especially those features in the low end of the signal range).

Background-Subtracted Signal Plot: Non-Control Inliers (for each channel)—this metric is shown as metric 260 in FIG. 1A, and plots background-subtracted signal (log scale) in plot of one channel versus the other (e.g., red vs. green). The linearity or curvature of this plot is an indicator of appropriateness of background method choices. Non-control (i.e. ControlType=0) probes that are inliers (i.e., neither non-uniform nor saturated) are plotted. If the global background adjust (GBA) algorithm is selected by user, the plot will also color-code two populations of features: (1) those features that are used to determine the central tendency of the data; (2) and those features that are used in the final calculation of the GBA values. These color-coded features are useful to qualitatively check the GBA algorithm.

Statistical Summaries of Features with respect to Background—may include number of features with a negative background-subtracted signal value, number of features that are positive and that are significantly different from background (e.g., with a significance p value less than or equal to a user-settable value, typically, 0.01), and number of features well above the background level, as determined by signal levels greater than a predetermined multiplier of standard deviation (e.g., greater than three times the standard deviation of the background used).

Background-Subtracted Signal Summary: Spike-In Controls Inliers—This metric is a measure of reproducibility at the lower signal end of dynamic range of the array, and may be used as an alternative to the metric just previously described when spike-in probes are present and the user has hybridized with target to the spike-in probes. Those spike-in probes that are present at 0.5 copy and those at 1.5 copies are selected and from this a S2BGUsed metric is calculated based on inliers of that probe sequence population (e.g. median of S2BGUsed for each of the two different spike-in probe sequences, as discussed above with regard to metric 360). These values will not be LLD's, rather, they are values at low signal, that can be tracked reproducibly by the user.

Sensitivity at Lower Signal Range—The present systems do not calculate Lower Limits of Detection ("LLD's"), rather, values at low signal are outputted that can be tracked reproducibly by the user and may be used as an alternative to the S2BGUsed metric discussed above, if spike-in probes are not present on the array being considered, or if the user has not hybridized with spike-in target. This metric requires that there be at least one probe sequence of the array with replicate features. Using the Signal to BackgroundUsed ratio (S2BGUsed) as described above, the probe sequence (having replicate features) with the lowest average background-subtracted signal, and that also has a median S2BGUsed ratio greater than or equal to a preset number (typically, 3, although different numerical values may be used) is identified. The probe sequence, average background-subtracted signal, and average S2BGUsed can be outputted.

High Signal Gradient (for each channel)—This metric may be useful in identifying whether there is a gradient in the high signal range (i.e. "multiplicative" type), and may be used to detect gradients caused by the presence of ozone ("ozone gradients"), for example. Center of gravity ("COG") measurements of high signals are calculated for each channel. The displacements of these COGs from the center of the array are calculated. "High signal" range may be defined in many manners; one example uses the upper 1% of features (log signal). In addition, a subset of features may be used for these calculations, such as features that are control type zero and inliers (neither non-uniform nor saturated). Also, the displacements of centers of gravity may be calculated across channels (i.e. from Red_COG to Green_COG). By examining patterns of these COG metrics, along with the RMS_Fit of the high signal gradient detected by the software, one may be able to diagnose problems such as hybridization artifacts (e.g., such as non-moving bubbles) and/or ozone exposure (which preferentially decreases signal in the red channel more than in the green channel).

Dye Normalization Summary—DyeNormFactors (DNF)—Linear dye normalization factors indicate the relative strength of the signal in each channel. Lowess DNF indicates how much Lowess curve-fitting was needed to normalize dye factors. Linear DNF may be outputted in statistics table 500. When using Lowess DNF, each feature has a value in the feature extraction textual output. For use as a QC metric (in statistics table 500 and/or QC report 100) the average of absolute difference from 1.0 is calculated with respect to control type 0 (i.e., non-control) features. Alternatively, a LowessRMS can be calculated by calculating the RMS (root mean squared) value of the Lowess DNF for all the probes around the mean Lowess DNF value.

Dye Normalization Summary—IsNorm—the IsNorm metric indicates how many features were used in the dye-normalization step. This metric may be useful when comparing different DyeNorm methods. Each feature is assigned a Boolean value (IsNorm=0 or 1) to indicate whether or not it was used by the feature extraction module for dye normalization processing. For use as a QC metric, the sum of all IsNorm values is calculated and outputted.

Error Model and Significant Log Ratios—Additive Error Values (AddErr, for each channel)—AddErr values indicate noise at low-signal range that was used in determining significance of log ratios.

Error Model and Significant Log Ratios—Number Significant Log Ratios—the number of significantly up-regulated and significantly down-regulated log ratios (for non-control (i.e., control type=0) inlier features), when additive error values are considered, may be calculated, outputted and tracked. As a QC metric, the number of significantly up-regulated log-ratios may be summed and the number of significantly down-regulated log ratios may be summed, as these sums may be outputted as QC metrics. A Log Ratios Signature Plot may also be outputted, with the values for Significant Log Ratios shown superimposed upon or below the plot (e.g., metrics 280 and 290). Further, the features used in dye normalization may be color-coded with a different color to distinguish them from features that were not used for dye normalization, to aid the user in assessing the effectiveness of the dye normalization algorithm used (both as to probe selection and to curve-fitting).

Error Model and Significant Log Ratios—Significant Log Ratios —Centers of Gravity (COG)—Centers of Gravity are calculated to determine if the COG of significant "up" features (based on findings of significantly up-regulated log ratios) is spatially different from center and/or different from the COG of significant "down" features (based on findings of significantly down-regulated log ratios), by determining the displacement between the COG for up features and the COG for down features. One example uses all non-control inlier features. Alternative one may use a group of positive controls inliers, such as spike-in probes, for example. Alternatively, two sets of COG's may be outputted, one from features that are at lower signal range (i.e. any displacement from center or difference between "up" and "down" would indicate problems at the "additive" level); and one from features that are at higher signal range (i.e. any displacement from center or difference between "up" and "down" would indicate problems at the "multiplicative" level). These metrics may also be useful in detecting gradients at high signal that may be indicative of hyb/wash problems (e.g., bubble-moving, not smooth or ozone problems, etc.).

Error Model and Significant Log Ratios—Significant Log Ratios—Spatial plot(s)—As a visual aid to determine if a log ratio gradient exists, features exhibiting log ratios that are significant (e.g., pValue<=0.01) may be selected for control type 0 features which are inliers (neither non-uniform nor saturated). These features are then plotted in row and column positions corresponding to their positions on the array, where significantly up ratios are plotted in a first color and significantly down ratios are plotted in a second color (e.g., metric 300). The plot may further indicated the COG for up features and COG for down features (by overlaying an "X" or other indicator for each). Alternatively, two plots may be generated, one showing those log ratios from features that are at lower signal range (i.e. any gradient would be at the "additive" level); and the other showing those log ratios from features that are at higher signal range (i.e. any gradient would be at the "multiplicative" level).

Log Ratios—Reproducibility—Replicate probes on catalog arrays (control type=0)—Use the S/N of log ratios of inlier features (neither non-uniform nor saturated). Calculate S/N's (population Avg/SD, as described above with regard to metric 346) for each probe sequence (e.g. for human catalog array: 10 replicates/sequence for each S/N; 100 sequences have replicates, thus, calculate 100 different S/N's). For a statistical metric, the average or median of the population of these calculated S/N values may be calculated and outputted. The average of the absolute of the average of Log Ratios may be calculated and outputted (see metric 342 above) to give an indication of amount of differential expression; up or down). A histogram of these results may also be plotted.

Log Ratios: Sensitivity—as noted earlier, LLD's will not be provided, but rather these metrics can be used for tracking.

Spike in probes—Specifically identified spike-in probes having expected low signal (e.g., nominally, 0.5 and 1.5 copy/cell) and expected Log Ratio of 1:3 or 3:1 may be used, with replicates, to calculate the following statistics for inliers of each of these two populations: Average of Log Ratio; and S/N of Log Ratios (for example, the eighth and ninth rows of the table of metric 400).

An alternative metric includes the use of all spike-in probes to interpolate a S/N value by calculating a population S/N (of inliers) of each spike-in probe with expected log ratio less than or greater than zero. For example, eight such sequences exist on the human array catalog. Absolute values of the calculated S/N values are then plotted against the absolute value of their expected absolute log ratio values. Then a minimum detectable expected absolute log ratio value is obtained by interpolation or extrapolation from the plot, to find the minimum detectable expected absolute log ratio that has a S/N value greater than or equal to a threshold value (e.g., greater than or equal to three).

If an array does not have spike-in probes, or if the user does not target to the spike-in probes, and if the array has replicate non-control probes, then the statistics described above can be calculated for interpolation with regard to inlier non-control probes that have replicates.

Figure 7:
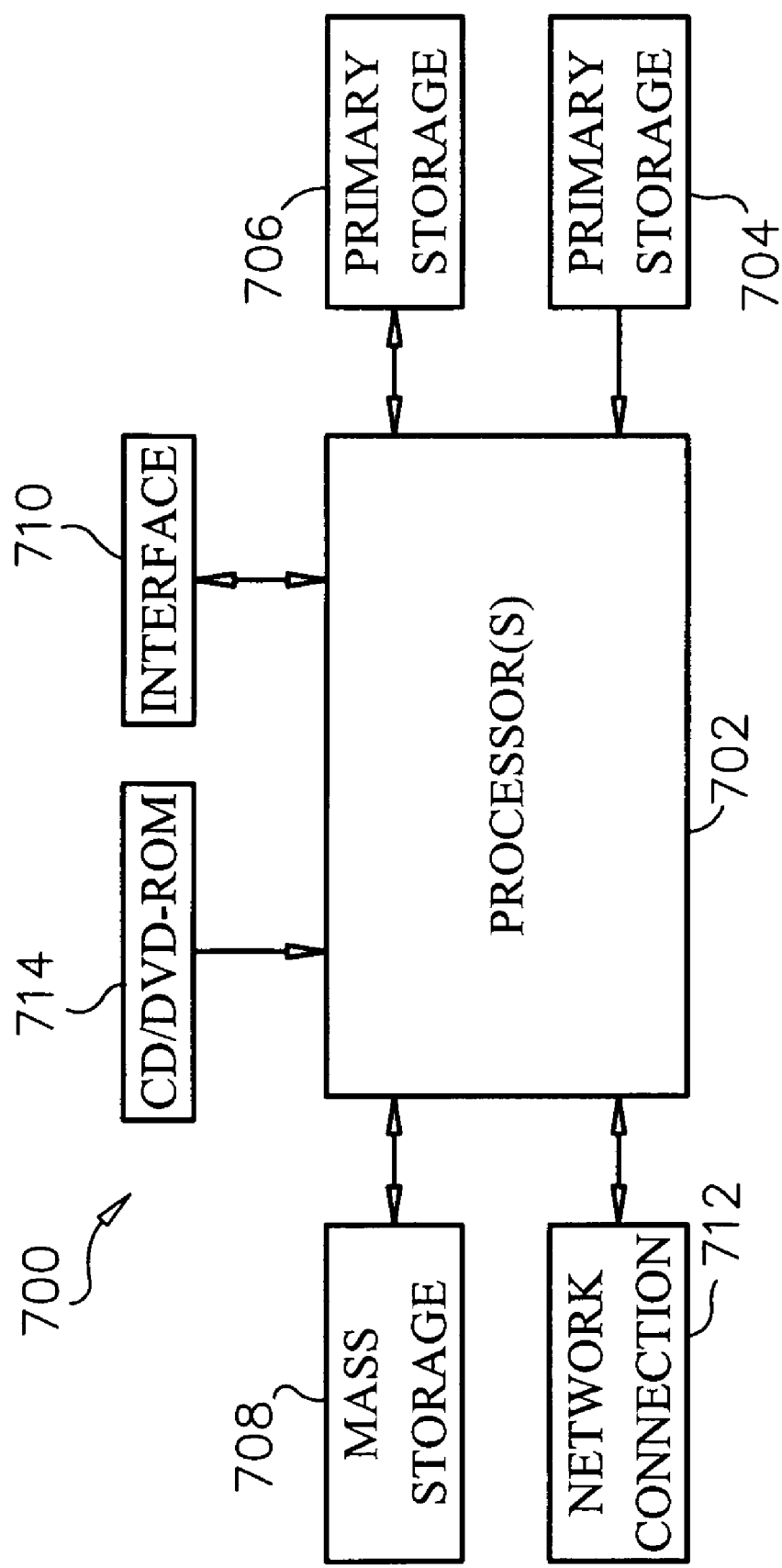
FIG. 7 illustrates a typical computer system in accordance with an embodiment of the present invention.

FIG. 7 illustrates a typical computer system in accordance with an embodiment of the present invention. The computer system 700 includes any number of processors 702 (also referred to as central processing units, or CPUs) that are coupled to storage devices including primary storage 706 (typically a random access memory, or RAM), primary storage 704 (typically a read only memory, or ROM). As is well known in the art, primary storage 704 acts to transfer data and instructions uni-directionally to the CPU and primary storage 706 is used typically to transfer data and instructions in a bi-directional manner Both of these primary storage devices may include any suitable computer-readable media such as those described above. A mass storage device 708 is also coupled bi-directionally to CPU 702 and provides additional data storage capacity and may include any of the computer-readable media described above. Mass storage device 708 may be used to store programs, data and the like and is typically a secondary storage medium such as a hard disk that is slower than primary storage. It will be appreciated that the information retained within the mass storage device 708, may, in appropriate cases, be incorporated in standard fashion as part of primary storage 706 as virtual memory. A specific mass storage device such as a CD-ROM or DVD-ROM 714 may also pass data uni-directionally to the CPU.

CPU 702 is also coupled to an interface 710 that includes one or more input/output devices such as video monitors, track balls, mice, keyboards, microphones, touch-sensitive displays, transducer card readers, magnetic or paper tape readers, tablets, styluses, voice or handwriting recognizers, or other well-known input devices such as, of course, other computers. Finally, CPU 702 optionally may be coupled to a computer or telecommunications network using a network connection as shown generally at 712. With such a network connection, it is contemplated that the CPU might receive information from the network, or might output information to the network in the course of performing the above-described method steps. The above-described devices and materials will be familiar to those of skill in the computer hardware and software arts.

The hardware elements described above may implement the instructions of multiple software modules for performing the operations of this invention. For example, instructions for calculating and plotting metrics may be stored on mass storage device 708 or 714 and executed on CPU 708 in conjunction with primary memory 706.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method comprising the steps of:
    generating at least one metric indicative of accuracy of location of features on a chemical array by a feature extraction process used to extract signals from features of the chemical array;
    generating at least one additional metric adapted to identify errors caused by a particular process used in generating the signals on the array;
    generating a quality control report containing said at least one metric indicative of accuracy of location and said at least one additional metric; and
    outputting said quality control report;
    wherein the process used in generating the signals is selected from the group consisting of array design process, array synthesis process, target preparation process, target labeling process, array hybridization process, washing process, stripping process, scanning process, feature extraction process, or a combination thereof.

2. The method of claim 1, wherein the at least one additional metric objectively identifies said errors by providing a numeric metric.

3. The method of claim 1, wherein said quality control report is generated in a quality control report file.

4. The method of claim 1, further comprising outputting said quality control report for visualization by a user.

5. The method of claim 1, further comprising generating additional metrics that do not appear in said quality control report and that characterize the chemical array; and
    generating a table containing said at least one metric indicative of accuracy of location; said at least one additional metric; and said additional metrics that do not appear in said quality control report.

6. The method of claim 5, wherein one of said additional metrics comprises multiplicative surface fit.

7. The method of claim 5, further comprising:
    customizing said quality control report by user selection comprising at least one of:
    selecting an additional metric from said table, not currently reported in said quality control report and generating said quality control report with the additional metric from said table;
    selecting an additional metric from said table, not currently reported in said quality control report to replace one of said at least one metric indicative of accuracy of location and said at least one additional metric, and generating said quality control report with the replacement; and
    selecting at least one of said at least one metric indicative of accuracy of location and said at least one additional metric to be omitted from said quality control report, and generating said quality control report with the omission.

8. The method of claim 5, further comprising tracking values of at least one of said metrics across multiple arrays and monitoring for significant variation of one or more of said values from other values generated by the same metric.

9. The method of claim 5, further comprising tracking values of at least one of said metrics at multiple periods of elapsed time and monitoring for significant variation of one or more of said values from other values generated by the same metric.

10. The method of claim 1, further comprising selecting a quality control report type to be generated, wherein said generating a quality control report includes generating a quality control report of the type selected.

11. The method of claim 10, wherein said quality control type is selected from at least one of: two-channel, single-channel, CGH, Gene Expression, and Location Analysis.

12. The method of claim 1, further comprising storing said metrics contained in said quality control report in a database for subsequent access by a user.

13. The method of claim 12, further comprising accessing the database; selecting at least a subset of said metrics stored in said database; and generating at least one run chart using data contained in said at least a subset.

14. The method of claim 12, further comprising storing additional user input in said database with said stored metrics to facilitate querying the database for selective retrieval of subsets of the stored metrics.

15. The method of claim 12, further comprising storing feature extraction parameters of arrays from which the stored metrics were generated, associated with said stored metrics in said database, to facilitate querying the database for selective retrieval of subsets of the stored metrics.

16. The method of claim 1, wherein the steps of claim 1 are repeated for at least one additional array.

17. The method of claim 16, further comprising generating a run summary that includes at least one of: at least one error statement, at least one warning statement, and summary information characterizing processing of said arrays.

18. The method of claim 17, further comprising customizing said run summary to show only those of said at least one error statement, at least one warning statement and summary information characterizing processing of said arrays that exceed a user-settable or calculatable threshold.

19. The method of claim 16, further comprising customizing said quality control report by user selection to show only metrics that exceed a user-settable threshold.

20. The method of claim 1, further comprising generating a run summary that includes at least one of: at least one error statement, at least one warning statement, and summary information characterizing processing of said array.

21. The method of claim 20, further comprising customizing said run summary to show only those of said at least one error statement, at least one warning statement and summary information characterizing processing of said array that exceed a user-settable or calculatable threshold.

22. The method of claim 1, further comprising customizing said quality control report by user selection to show only metrics that exceed a user-settable or calculatable threshold.

23. The method of claim 1, further comprising generating header information for said quality control report and wherein said quality control report is generated to include said header information.

24. The method of claim 23, wherein said header information comprises a visualization identifying the array and properties of characterizing extraction of the array.

25. The method of claim 24, wherein said header information includes at least one of a date that extraction was performed and said QC report 100 was generated, a time stamp, identification of the array image, feature extraction protocol, user that performed the extraction, feature extraction module or software used, grid used, background correction method used, whether or not spatial de-trending was used, whether or not a global background adjust algorithm was used, type of dye normalization correction method used, linear dye-normalization factors used, and additive error values used.

26. The method of claim 23, further comprising customizing said header information by user selection to perform at least one of addition, deletion and substitution of information contained in said header information.

27. The method of claim 1, wherein at least one of said at least one metric indicative of location of features and said at least one additional metric comprises a graphical visualization.

28. The method of claim 27, wherein said graphic visualization display a composite image of four corner sections of the chemical array.

29. The method of claim 1, wherein generating at least one metric indicative of accuracy of location of features comprises a goodness of fit numeric metric.

30. The method of claim 1, further setting of at least one threshold value by a user relative to at least one of said metrics, and indicating in said quality control report when said at least one of said metrics crosses said at least one threshold, respectively.

31. The method of claim 30, further comprising dynamically adjusting at least one of said at least one threshold values by a user based on processing results achieved from processing a plurality of chemical arrays using said steps.

32. The method of claim 1, further comprising automatically flagging at least one of non-uniform features and population outliers generated during processing of the chemical array, and excluding at least one of said non-uniform features and said population outliers from consideration when generating at least one of said at least one additional metric.

33. The method of claim 1, wherein said generating at least one additional metric is performed considering only a specified subset of probes on the chemical array.

34. The method of claim 33, wherein said specified subset of probes is selected from the group consisting of positive controls, negative controls, spike-in controls, experimental probes and combinations thereof.

35. The method of claim 1, further comprising automatically determining at least one of at least one of non-uniform features and population outliers; and plotting at least one of said non-uniform features and said population outliers in said quality control report.

36. The method of claim 1, further comprising automatically determining at least one of at least one of non-uniform features and population outliers; and displaying a quantitative report of at least one of said non-uniform features and said population outliers in said quality control report.

37. The method of claim 1, wherein one or more metrics generated by said generating at least one additional metric are generated based a protocol used in extracting the chemical array.

38. The method of claim 37, wherein the protocol used in extracting the chemical array is selected from the group consisting of CGH protocol, location analysis protocol and gene expression protocol, and wherein the chemical array is further characterized by one of the following: single-channel array, two-channel array and multiple-channel array having more than two channels.

39. The method of claim 1, wherein at least one of said metrics identifies a non-specific processing error, said method further comprising identifying a specific processing error based at least in part on said non-specific processing error.

40. The method of claim 1, wherein said generating at least one additional metric includes generating a signature plot and plotting said signature plot in said quality control report.

41. The method of claim 40, wherein said signature plot plots log ratio values of feature signals versus an average log signal value.

42. The method of claim 40, wherein said signature plot plots only log ratio signal values of non-control feature signals.

43. The method of claim 1, wherein said generating at least one additional metric comprises calculating spike-in signal to background signal ratio values.

44. The method of claim 1, wherein said generating at least one additional metric comprises calculating net signals from probes of a single channel array scanning system, wherein a plot of distribution of the logs of said net signals is provided in said quality control report.

45. The method of claim 1, wherein said generating at least one additional metric comprises calculating spatial distribution of median signals for each row and column on the array, wherein a plot of said median signal versus row and a plot of said median signal versus column is provided in said quality control report.

46. The method of claim 1, wherein said generating at least one additional metric comprises calculating the signal of spike-in probes versus relative concentration, wherein a said signal versus said relative concentration is plotted in said quality control report.

47. The method of claim 1, further comprising determining a sensitivity metric by a user, based on at least one of said metrics generated.

48. A method of generating a customized quality control report, said method comprising:
    user selection of at least one metric adapted to identify errors caused by a particular process used in generating signals on a chemical array, said at least one selection being selected from a plurality of metrics;
    generating a quality control report containing said at least one user-selected metric; and
    outputting said quality control report, wherein a default set of metrics is also included and contained in said quality control report.

49. The method of claim 48, said method further comprising user selection of at least one metric in said default set of metrics to be omitted from said quality control report, wherein said generating said quality control report comprises generating said quality control report to omit said at least one default metric having been selected for omission.

50. The system of claim 49, wherein said user interface is further configured for interactive user modification of header information to be displayed in said quality control report.

51. The system of claim 50, wherein said user interface is further configured for user selection of at least one of metrics, error messages and warnings to be displayed in a run summary.

52. The system of claim 50, wherein said user interface is further configured for user selection of a minimum number of replicate probes required to perform summary statistics.

53. The system of claim 50, wherein said user interface is further configured for user customization of filters.

54. The method of claim 48, further comprising at least one of user addition of header information to be displayed in a header of said quality control report and user selection of existing header information to be omitted from said header, wherein upon said generation of said quality control report, said header displays said addition and omits said information selected to be omitted.

55. A system for characterizing a chemical array, said system comprising:
    means for generating metrics from feature extraction outputs, said metrics adapted to identify errors caused by a particular process used in generating the signals on the array;
    means for generating a quality control report containing at least one of said metrics; and
    means for outputting said quality control report;
    wherein the process used in generating the signals is selected from the group consisting of array design process, array synthesis process, target preparation process, target labeling process, array hybridization process, washing process, stripping process, scanning process, feature extraction process, or a combination thereof.

56. The system of claim 55, further comprising a user interface configured for interactive user selection of at least one of said metrics to be contained in said quality control report.

57. The system of claim 56, wherein said user interface is further configured for interactive user setting of at least one threshold value relative to at least one of said metrics.

58. A computer readable medium comprising at least one of: a storage disk, hard disk, floppy disk, CD, DVD or flash memory storage device carrying one or more sequences of instructions for characterizing a chemical array, wherein execution of one or more sequences of instructions by one or more processors causes the one or more processors to perform the steps of:
    generating metrics adapted to identify errors caused by a particular process used in generating the signals on the array;
    generating a quality control report containing at least one of said metrics; and
    outputting said quality control report;
    wherein the process used in generating the signals is selected from the group consisting of array design process, array synthesis process, target preparation process, target labeling process, array hybridization process, washing process, stripping process, scanning process, feature extraction process, or a combination thereof.

59. A method comprising the steps of:
    generating at least one metric indicative of accuracy of location of features on a chemical array by a feature extraction process used to extract signals from features of the chemical array;
    generating at least one additional metric adapted to identify errors caused by a particular process used in generating the signals on the array;
    generating a quality control report containing said at least one metric indicative of accuracy of location and said at least one additional metric;
    outputting said quality control report;
    generating additional metrics that do not appear in said quality control report and that characterize the chemical array; and generating a table containing said at least one metric indicative of accuracy of location; said at least one additional metric; and said additional metrics that do not appear in said quality control report.

60. A method comprising the steps of:

generating at least one metric indicative of accuracy of location of features on a chemical array by a feature extraction process used to extract signals from features of the chemical array;

generating at least one additional metric adapted to identify errors caused by a particular process used in generating the signals on the array;

generating a quality control report containing said at least one metric indicative of accuracy of location and said at least one additional metric;

outputting said quality control report; and generating a run summary that includes at least one of: at least one error statement, at least one warning statement, and summary information characterizing processing of said array.

61. A method comprising the steps of:

generating at least one metric indicative of accuracy of location of features on a chemical array by a feature extraction process used to extract signals from features of the chemical array;

generating at least one additional metric adapted to identify errors caused by a particular process used in generating the signals on the array;

generating a quality control report containing said at least one metric indicative of accuracy of location and said at least one additional metric; and outputting said quality control report;

wherein at least one of said at least one metric indicative of location of features and said at least one additional metric comprises a graphical visualization.

* * * * *